United States Patent
LaBorde

(10) Patent No.: US 11,961,619 B1
(45) Date of Patent: *Apr. 16, 2024

(54) SYSTEM, METHOD AND DEVICE FOR PREDICTING NEED FOR SURGICAL INTERVENTION

(71) Applicant: Brain Trust Innovations I, LLC, Alpharetta, GA (US)

(72) Inventor: David LaBorde, Alpharetta, GA (US)

(73) Assignee: Brain Trust Innovations I, LLC, Alpharetta, GA (US)

( * ) Notice: Subject to any disclaimer, the term of this patent is extended or adjusted under 35 U.S.C. 154(b) by 791 days.

This patent is subject to a terminal disclaimer.

(21) Appl. No.: 16/139,584

(22) Filed: Sep. 24, 2018

Related U.S. Application Data

(60) Provisional application No. 62/575,332, filed on Oct. 20, 2017.

(51) Int. Cl.
- *G06N 3/04* (2023.01)
- *G06N 3/02* (2006.01)
- *G06N 3/08* (2023.01)
- *G16H 50/20* (2018.01)
- *G16H 50/30* (2018.01)
- *G16H 30/40* (2018.01)

(52) U.S. Cl.
CPC .............. *G16H 50/30* (2018.01); *G06N 3/02* (2013.01); *G16H 50/20* (2018.01); *G16H 30/40* (2018.01)

(58) Field of Classification Search
CPC ......... G16H 50/20; G16H 50/30; G16H 10/60
See application file for complete search history.

(56) References Cited

U.S. PATENT DOCUMENTS

| | | | | |
|---|---|---|---|---|
| 7,852,221 | B2 * | 12/2010 | Tuttle | G06K 19/07749 340/10.3 |
| 8,181,875 | B2 * | 5/2012 | Nishido | G06K 19/0701 340/572.1 |
| 9,569,589 | B1 | 2/2017 | Laborde | |
| 9,679,108 | B1 | 6/2017 | Laborde | |
| 9,848,827 | B1 | 12/2017 | Laborde | |
| 9,928,342 | B1 | 3/2018 | Laborde | |
| 9,943,268 | B1 | 4/2018 | Laborde | |
| 9,977,865 | B1 | 5/2018 | Laborde | |
| 9,980,681 | B1 | 5/2018 | Laborde | |
| 10,014,076 | B1 | 7/2018 | Laborde | |
| 10,026,506 | B1 | 7/2018 | Laborde | |

(Continued)

OTHER PUBLICATIONS

Sasank Chilamkurthy et al., "Automated Detection of Intra- and Extra-Axial Haemorrhages on CT Brain Images Using Deep Neural Networks", Mar. 4, 2018, European Congress of Radiology.

(Continued)

*Primary Examiner* — Reginald R Reyes
(74) *Attorney, Agent, or Firm* — Culpepper IP, LLLC; Kerry S. Culpepper

(57) ABSTRACT

A system that includes data collection engine devices, client devices and backend devices. The backend devices include trained models, business logic, and attributes of a plurality of patient events. A plurality of data collection engines and hospital information systems send input attributes of new patient events to the backend devices. The backend devices can predict particular outcomes of new patient events based upon the input attributes utilizing the trained models.

16 Claims, 35 Drawing Sheets

(56) References Cited

U.S. PATENT DOCUMENTS

| | | | |
|---|---|---|---|
| 10,028,707 | B1 | 7/2018 | Laborde |
| 10,043,591 | B1 | 8/2018 | Laborde |
| 10,043,592 | B1 | 8/2018 | Laborde |
| 10,319,476 | B1* | 6/2019 | LaBorde .............. G06N 3/08 |
| 2006/0129427 | A1* | 6/2006 | Wennberg .......... G06Q 10/00 703/2 |
| 2011/0291809 | A1* | 12/2011 | Niemiec .............. H02M 7/003 206/528 |

OTHER PUBLICATIONS

Mustafa Bivijii et al., "Deep Neural Networks to Identify and Localize Intracerebral Hemorrhage and Midline Shift in CT Scans of Brain", Nov. 26, 2017, Radiological Society of North America.
Wenan Chen et al., "Automated Midline Shift and Intracranial Pressure Estimation based on Brain CT Images", Apr. 13, 2013.
Kaiming He et al., "Delving Deep into Rectifiers: Surpassing Human-Level Performance on ImageNet Classification", Feb. 6, 2015, Microsoft Research.
Sasank Chilamkurthy et al., "Development and Validation of Deep Learning Algorithms for Detection of Critical Findings in Head CT Scans", Apr. 12, 2017.
Chun-Chi Liao et al., "Brain Midline Shift Measurement and Its Automation: A Review of Techniques and Algorithms", Apr. 12, 2018, International Journal of Biomedical Imaging, vol. 2018, Article ID 4303161.
"Algebraic Reconstruction Algorithms"; Lee W. Goldman.
Uwe Joseph Schoepf et al., "State of the Art: Iterative CT Reconstruction Techniques", Aug. 2015.
Adnan Nabeel Abid Qureshi, "Computer Aided Assessment of CT Scans of Traumatic Brain Injury Patients" (Doctoral Thesis), [online], 2015[retrieved on Sep. 20, 2018]. Retrieved from the Internet: <URL: http://uobrep.openrepository.com/uobrep/handle/10547/601083 >.
Xuguang Qi et al., "Automated Intracranial Pressure Prediction Using Multiple Features Sources," 2013 International Conference on Information Science and Applications (ICISA), Suwon, Korea (South) Korea (South), 2013, pp. 1-4.
Ruizhe Liu, "Automatic Quantification of Brain Midline Shift in CT Images" (Doctoral Thesis), [online], 2012 [retrieved on Sep. 20, 2018]. Retrieved from the Internet: <URL: https://scholarbank.nus.edu.sg/bitstream/10635/31586/1/LiuRZ.pdf>.
Monika Grewal et al., "RADnet: Radiologist Level Accuracy Using Deep Learning for Hemorrhage Detection in CT Scans," IEEE Symposium on Biomedical Imaging (ISBI) 2018, Washington District of Columbia, arXiv:1710.04934v2, Jan. 3, 2018.
Rikiya Yamashita et al., "Convolutional Neural Networks: An Overview and Application in Radiology," Insights Imaging, 2018, 9: 611.
Chris Rorden, Ph.D., "The DICOM Standard", [online] [retrieved on Sep. 20, 2018]. Retrieved from the Internet: <URL: http://people.cas.sc.edu/rorden/dicom/index.html>.
Yao Wang, Ph.D., "Computed Tomography (Part I)", [online] [retrieved on Sep. 20, 2018]. Retrieved from the Internet: <URL: http://eeweb.poly.edu/~yao/EL5823/CT_ch6_part1.pdf>.
Yao Wang, Ph.D., "Computed Tomography (Part II)", [online] [retrieved on Sep. 20, 2018]. Retrieved from the Internet: <URL: http://eeweb.poly.edu/~yao/EL5823/CT_ch6_part2.pdf>.
Guido Zuidhof, "Full Preprocessing Tutorial," [online] [retrieved on Sep. 20, 2018]. Retrieved from the Internet: <URL: https://www.kaggle.com/gzuidhof/full-preprocessing-tutorial>.
Annelies van der Plas "X-ray/CT technique," [online] Mar. 17, 2014 [retrieved on Sep. 20, 2018]. Retrieved from the Internet: <URL: http://www.startradiology.com/the-basics/x-rayct-technique/>.
Bhanupria Singh, "Physical Principals of CT," [online], Jan. 11, 2016 [retrieved on Sep. 20, 2018]. Retrieved from the Internet: <URL: https://www.slideshare.net/bhanupriyasingh03/ct-physics-56917968>.
The University of Texas High-Resolution X-ray Computed Tomography Facility, "Acquisition of CT Data," [online], 2016 [retrieved on Sep. 20, 2018]. Retrieved from the Internet: <URL: http://www.ctlab.geo.utexas.edu/about-ct/acquisition-of-ct-data/>.
Rituraj Mishra, BSc.MIT, "Computed Tomography: Basic Principle and Its Generations" Jan. 22, 2017 [retrieved on Sep. 20, 2018]. Retrieved from the Internet: <URL: https://www.slideshare.net/RiturajMishra11/computed-tomography-71255186?next_slideshow=1>.
Dandu Ravi Varma, "Managing DICOM images: Tips and tricks for the radiologist," Indian J Radiol Imaging. Jan.-Mar. 2012; 22(1): 4-13. pydicom.
"Working with Pixel Data," [online] [retrieved on Sep. 20, 2018]. Retrieved from the Internet: <URL: https://pydicom.github.io/pydicom/stable/working_with_pixel_data.html>.
Matt McCormick, "DICOM Rescale Intercept / Rescale Slope and ITK" [online], [retrieved on Sep. 20, 2018]. Retrieved from the Internet: <URL: https://blog.kitware.com/dicom-rescale-intercept-rescale-slope-and-itk/>.
Wikipedia, "Hounsfield Scale" [online], [retrieved on Sep. 20, 2018]. Retrieved from the Internet: <URL: https://en.wikipedia.org/wiki/Hounsfield_scale>.
Wikipedia, "Computed tomography of the head" [online], [retrieved on Sep. 20, 2018]. Retrieved from the Internet: <URL: https://en.wikipedia.org/wiki/Computed_tomography_of_the_head>.
Tanay Kothari. "Superman isn't the only one with X-Ray vision: Deep Learning for CT Scans" [online], Feb. 5, 2018 [retrieved on Sep. 20, 2018]. Retrieved from the Internet: <URL: https://medium.com/stanford-ai-for-healthcare/superman-isnt-the-only-one-with-x-ray-vision-deep-learning-for-ct-scans-290aaa7ba5c1>.
Dr Daniel J Bell et al, "Windowing (CT)," [online], [retrieved on Sep. 20, 2018]. Retrieved from the Internet: <URL: https://radiopaedia.org/articles/windowing-ct>.
Bryan Taylor, "What is zero-centering (data preprocessing technique)? "[online], [retrieved on Sep. 20, 2018]. Retrieved from the Internet: <URL: https://www.quora.com/What-is-zero-centering-data-preprocessing-technique>.
"Principles of CT and CT Technology", May 7, 2007, J. Nucl. Med. Technol. 2007, 35:115-128.
Greg Michael, "X-Ray Computed Tomography," Medical Physics, Physics Education 2001, 36:442-451.

* cited by examiner

Data Fields/Properties

|  | Property 1 | Property 2 | Property 3 | ... | Property N |
|---|---|---|---|---|---|
| Data 1 |  |  |  |  |  |
| Data 2 |  |  |  |  |  |
| Data 3 |  |  |  |  |  |
| ... |  |  |  |  |  |
| Data N |  |  |  |  |  |

Collected Data

FIG. 11B

SYSTEM, METHOD AND DEVICE FOR PREDICTING NEED FOR SURGICAL INTERVENTION

CROSS-REFERENCE TO RELATED APPLICATIONS

The present application claims the benefit of U.S. Provisional Patent Application No. 62/575,332 filed on Oct. 20, 2017, the contents of which are incorporated herein by reference.

The present application incorporates by reference the contents of: Sasank Chilamkurthy et al., "Automated Detection of Intra- and Extra-Axial Haemorrhages On CT Brain Images Using Deep Neural Networks", Mar. 4, 2018, European Congress of Radiology; Mustafa Bivijii et al., "Deep Neural Networks to Identify and Localize Intracerebral Hemorrhage and Midline Shift in CT Scans of Brain", Nov. 26, 2017, Radiological Society of North America; Wenan Chen et al., "Automated Midline Shift and Intracranial Pressure Estimation based on Brain CT Images", Apr. 13, 2013; Kaiming He et al., "Delving Deep into Rectifiers: Surpassing Human-Level Performance on ImageNet Classification", Feb. 6, 2015, Microsoft Research; Sasank Chilamkurthy et al., "Development and Validation of Deep Learning Algorithms for Detection of Critical Findings in Head CT Scans", Apr. 12, 2017; Chun-Chi Liao et al., "Brain Midline Shift Measurement and Its Automation: A Review of Techniques and Algorithms", Apr. 12, 2018, International Journal of Biomedical Imaging, Volume 2018, Article ID 4303161; "Algebraic Reconstruction Algorithms"; Lee W. Goldman, "Principles of CT and CT Technology", May 7, 2007, J. Nucl. Med. Technol. 2007, 35:115-128; Uwe Joseph Schoepf et al., "State of the Art: Iterative CT Reconstruction Techniques", August 2015; Adnan Nabeel Abid Qureshi, "Computer Aided Assessment of CT Scans of Traumatic Brain Injury Patients" (Doctoral Thesis), [online], 2015 [retrieved on 20 Sep. 2018]. Retrieved from the Internet: <URL: http://uobrep.openrepository.com/uobrep/handle/10547/601083>; Xuguang Qi et al., "Automated Intracranial Pressure Prediction Using Multiple Features Sources," 2013 International Conference on Information Science and Applications (ICISA), Suwon, Korea (South) Korea (South), 2013, pp. 1-4; Ruizhe Liu, "Automatic Quantification of Brain Midline Shift in CT Images" (Doctoral Thesis), [online], 2012 [retrieved on 20 Sep. 2018]. Retrieved from the Internet: <URL: https://scholarbank.nus.edu.sg/bitstream/10635/31586/1/LiuRZ.pdf>; Monika Grewal et al., "RADnet: Radiologist Level Accuracy Using Deep Learning for Hemorrhage Detection in CT Scans," IEEE Symposium on Biomedical Imaging (ISBI) 2018, Washington District of Columbia, arXiv:1710.04934v2, Jan. 3 2018; Rikiya Yamashita et al., "Convolutional Neural Networks: An Overview and Application in Radiology," Insights Imaging, 2018, 9: 611; Chris Rorden, Ph.D., "The DICOM Standard", [online] [retrieved on 20 Sep. 2018]. Retrieved from the Internet: <URL: http://people.cas.sc.edu/rorden/dicom/index.html>; Yao Wang, Ph.D., "Computed Tomography (Part I)", [online] [retrieved on 20 Sep. 2018]. Retrieved from the Internet: <URL: http://eeweb.poly.edu/~yao/EL5823/CT_ch6_part1.pdf>; Yao Wang, Ph.D., "Computed Tomography (Part II)", [online] [retrieved on 20 Sep. 2018]. Retrieved from the Internet: <URL: http://eeweb.poly.eduhyao/EL5823/CT_ch6_part2.pdf>; Guido Zuidhof, "Full Preprocessing Tutorial," [online] [retrieved on 20 Sep. 2018]. Retrieved from the Internet: <URL: https://www.kaggle.com/gzuidhof/full-preprocessing-tutorial>; Greg Michael, "X-Ray Computed Tomography," Medical Physics, Physics Education 2001, 36:442-451; StartRadiology, "X-ray/CT technique," [online] [retrieved on 20 Sep. 2018]. Retrieved from the Internet: <URL: http://www.startradiology.com/the-basics/x-rayct-technique/>; Bhanupria Singh, "Physical Principals of CT," [online], Jan. 11, 2016 [retrieved on 20 Sep. 2018]. Retrieved from the Internet: <URL: https://www.slideshare.net/bhanupriyasingh03/ct-physics-56917968>; The University of Texas High-Resolution X-ray Computed Tomography Facility, "Acquisition of CT Data," [online], 2016 [retrieved on 20 Sep. 2018]. Retrieved from the Internet: <URL: http://www.ctlab.geo.utexas.edu/about-ct/acquisition-of-ct-data/>; Rituraj Mishra, BSc.MIT, "Computed Tomography: Basic Principle and Its Generations" Jan. 22, 2017 [retrieved on 20 Sep. 2018]. Retrieved from the Internet: <URL: https://www.slideshare.net/RiturajMishra11/computed-tomography-71255186?next_slideshow=1>; "Dandu Ravi Varma, "Managing DICOM images: Tips and tricks for the radiologist," Indian J Radiol Imaging. 2012 January-March; 22(1): 4-13. pydicom, "Working with Pixel Data," [online] [retrieved on 20 Sep. 2018]. Retrieved from the Internet: <URL: https://pydicom.github.io/pydicom/stable/working_with_pixel_data.htm l>; and Matt McCormick, "DICOM Rescale Intercept/Rescale Slope and ITK" [online], [retrieved on 20 Sep. 2018]. Retrieved from the Internet: <URL: https://blog.kitware.com/dicom-rescale-intercept-rescale-slope-and-itk/>; Wikipedia, "Hounsfield Scale" [online], [retrieved on 20 Sep. 2018]. Retrieved from the Internet: <URL: https://en.wikipedia.org/wiki/Hounsfield_scale>; Wikipedia, "Computed tomography of the head" [online], [retrieved on 20 Sep. 2018]. Retrieved from the Internet: <URL: https://en.wikipedia.org/wiki/Computed_tomography_of_the_head>; Tanay Kothari. "Superman isn't the only one with X-Ray vision: Deep Learning for CT Scans" [online], Feb. 5, 2018 [retrieved on 20 Sep. 2018]. Retrieved from the Internet: <URL: https://medium.com/stanford-ai-for-healthcare/superman-isnt-the-only-one-with-x-ray-vision-deep-learning-for-ct-scans-290aaa7ba5c1>; Dr Daniel J Bell et al, "Windowing (CT)," [online], [retrieved on 20 Sep. 2018]. Retrieved from the Internet: <URL: https://radiopaedia.org/articles/windowing-ct>; and Bryan Taylor, "What is zero-centering (data preprocessing technique)?" [online], [retrieved on 20 Sep. 2018]. Retrieved from the Internet: <URL: https://www.quora.com/What-is-zero-centering-data-preprocessing-technique>.

TECHNICAL FIELD

The technical field generally relates to a system including a device receiving imaging data such as computed tomography scan images associated with a patient event, a data collection engine, a server device and a client device, and, more particularly, to a system that utilizes artificial intelligence techniques for predicting an outcome associated with the patient event.

BACKGROUND

Healthcare systems are complex operations in which throughput can be a major factor in the ability to accomplish goals, achieve and maintain financially solvency, and deliver a service level consistent with the expectations of customers or patients and employees, among other things. Delays or bottlenecks can have an adverse impact on throughput and reduce the performance of the healthcare system.

Artificial Intelligence (AI) technologies such as machine learning and deep learning have become ever present due to technological advances in data storage and processing. Machine learning at its most basic is the practice of using algorithms to parse data, learn from it, and then make a determination or prediction about something in the world. So rather than hand-coding software routines with a specific set of instructions to accomplish a particular task, the machine is "trained" using large amounts of data and algorithms that give it the ability to learn how to perform the task. Deep learning involves neural networks inspired by our understanding of the biology of our brains all those interconnections between the neurons. But, unlike a biological brain where any neuron can connect to any other neuron within a certain physical distance, these artificial neural networks have discrete layers, connections, and directions of data propagation.

SUMMARY

Valuable time can be lost during surgical emergencies for a variety of reasons. Exemplary reasons include: delays with interpretation of the imaging study by a radiologist or surgeon; delays with transmitting the radiology findings/interpretation of the image; delays in getting surgical team access to actually view the images; delays in arranging transport to another facility if the requisite surgical expertise is not available at the originating facility; overwhelmed physician staff at medical facilities; and delays in communication (i.e. returning of pages, etc.).

Delays in surgical intervention when a patient emergently requires surgery can result in poor outcomes. Neurological surgery is one such specialty where the timely determination of whether a patient requires surgical intervention can have a significant impact on outcomes.

Moreover, often interpretations made by radiologists or emergency medicine physicians or other providers can be inaccurate, in some cases being false positives and in others being false negatives, as it pertains to the necessity for emergent surgical intervention.

These providers are typically the first medical professionals to assess patients and provide their imaging findings in emergent situations. Therefore, the more accurate and timelier their assessments are and, more importantly, the more rapidly the surgical team is notified of cases that truly need emergent surgical intervention, the better.

In view of the above problems, as well as other concerns, the present disclosure concerns a method and system that utilizes artificial intelligence to make predictions based upon input patient attributes of patient events such as imaging studies of a patient. The prediction can be that the patient event warrants emergent surgical intervention.

The system learns from input patient attributes of historical patient events in which patients were presented to medical facilities and some ultimately underwent emergent surgical intervention and others did not undergo surgical intervention. Example input patient attributes include patient imaging studies, history of present illness, patient history, patient exam findings, patient lab findings, patient vital findings, other patient study results, etc. Particularly, the system trains models using machine learning algorithms based upon the patient attributes of the historical patient events. The system can then use the trained models to make predictions of the likelihood that a new patient event processed is consistent with a patient that does or does not require emergent surgical intervention.

The system can be deployed in one or more data centers and/or on one or more devices and integrated into the requisite hospital information systems (DICOM imaging data feed, radiology information system, electronic health records system, emergency department information system, and other hospital information systems).

During a patient event in which a patient is presenting to a medical facility, input patient attributes, such as, for example, image files (DICOM images) and other data are collected by the system via polling, event driven messaging, etc. The system performs any pre-processing on the patient attributes and stores the patient attributes in one or more databases. The patient attributes are then presented to a trained model to make a prediction of, for example, whether or not the patient needs surgical intervention. The prediction can be broadcast (transmitted over a network) encrypted or unencrypted with or without Imaging Study or Other Data to notification feed subscribers via wired or wireless connection over a network to end user client devices. Notifications to subscribers may be provided with a synopsis of the system's predictive model(s)' findings (i.e. new likely surgical lesion or new likely non-surgical lesion) with or without the related imaging and Other Data (i.e. protected health information), and/or may include a link to the record/patient/imaging study/Other Data/system's predictive model(s)' findings which can be followed/clicked to permit navigation to the information, upon successful authentication and authorization (via one of any number of methodologies) of the end user.

Once authenticated and authorized to access the data, the system allows end users to view the information (decrypted if encrypted for security during transmission), navigate to an image viewer (i.e. DICOM image viewer) where imaging study can be securely viewed on the end user client device. End users receiving notifications can also securely view on the system's end user client devices Other Data and information about the patient case and the output from the trained models (predicted surgical or non-surgical nature of the imaging study/patient case).

Notifications may be consumed by other machines or human non-clinical end users (i.e. administrators, managers, care coordinators, transporters, dispatchers, etc.) such as machines or humans in transfer centers at sending and or receiving hospitals, transportation providers such as ambulance services providers or life flight services providers, etc. (i.e. in case where originating facility does not have requisite surgical services and/or personnel available).

Examples of patient events that the system could be employed to assess include, but are not limited to, patients such as a trauma patient status post a fall with head trauma or status post a motor vehicle accident that undergoes a computed tomography (CT) scan of the head (may be found to have a subdural or epidural hematoma requiring surgical intervention) or a similar patient with that has undergone a CT scan of the cervical, thoracic and/or lumbar spine+/−an MRI of the cervical, thoracic and/or lumbar spine with and/or without Gadolinium (may harbor an acute spine fracture that requires surgical intervention).

The system can be deployed for a single tenant (enterprise or private cloud deployment) and/or shared across multiple facilities (multi-tenant cloud deployment).

The system may include a data collection engine (DCE) for collecting input patient attributes of a patient event and sending them to backend devices such as a server device, which inputs the patient attributes into the trained model to obtain the prediction. The DCE includes a transceiver, a controller operatively coupled to the transceiver, and a memory including instructions for configuring the controller. The transceiver can communicate with the server device via a connection to a network such as a LAN, the Internet, or cellular network. The controller is configured to generate messages to be sent by the transceiver to the server device. The DCE can also communicate with a client device such as a smartphone or a work station.

The server device includes a transceiver, a controller coupled to the transceiver, and memory portions including instructions for configuring the controller and providing one or more databases.

According to a first embodiment, the memory in the server device can include instructions for configuring the controller to: create a neural network model (NNM) for modeling patient events; train and validate the NNM by supervised learning; and calculate a predictive outcome for new patient events based upon the trained NNM.

The NNM includes an input layer, one or more hidden layers and an output layer. The input layer includes a number of input neurons in accordance with the plurality of input attributes, the output layer including a number of output neurons in accordance with the quantifiable outcome, and each of the one or more hidden layers including a number of hidden layers and possibly a bias neuron. The controller is configured to initialize values of a plurality of synaptic weights of the NNM to random values and perform pre-processing of the past patient transactions, including input attributes and outcomes, consisting of zero or multiple steps (a plurality) including, but not limited to normalization and/or dimensionality reduction. Next, the plurality of past patient events are divided into a first set of training data and a second set of validation data.

To train the NNM, the controller iteratively performs a machine learning algorithm (MLA) to adjust the values of the synaptic weights until a global error of an output of the NNM is below a predetermined acceptable global error, wherein each of the output values represents a calculated quantifiable outcome of the respective patient event. Performing the MLA includes: generating an output value of the NNM for each past patient event of the training data based upon the input attributes; measuring the global error of the NNM based upon the output values of the NNM and the quantifiable outcomes of the past patient event; and adjusting the values of the synaptic weights if the measured global error is not less than the predetermined acceptable global error to thereby obtain a trained NNM. Here, if the global error is never reached after number of outcomes, the model can be revised, such as number of hidden layers, neurons, etc.

To validate the NNM, the controller generates an output value of the trained NNM for each past patient event of the validation data, wherein each of the output values represents a calculated quantifiable outcome of the respective patient event; and determines if the output values correspond to the quantifiable outcome within the predetermined global error.

The creation and training of the NNM can be repeated until validation data results are satisfactory, defined as output data from the NNM being within the acceptable level of global error from the output values in the validation data set.

To calculate the outcome for new patient events based upon the trained NNM, the controller conducts pre-processing of input attributes of the new clinical patient event; and generates an output value of the trained NNM based upon the input attributes of the new clinical patient event.

The patient event can be a plurality of CT scanning images. The input patient attributes can be Hounsfield units associated with the CT scanning images. Pre-processing can include taking an array of sliced passes from the CT scanning images and returning an array of the CT scan slices with intensity values for each pixel.

According to a second embodiment, the instructions configure the controller to create a self-organizing map (SOM) network for modeling patient events, the SOM including a plurality of network nodes, a plurality of input nodes representing input attributes of the past patient events, wherein the plurality of network nodes is arranged in a grid or lattice in a fixed topological position, each of the plurality of input nodes is connected to all of the plurality of network nodes by a plurality of synaptic weights. Creating the SOM network includes: initializing values of the plurality of synaptic weights to random values; randomly selecting one past patient event and determining which of the plurality of network nodes is a best matching unit (BMU) according to a discriminant function, wherein the discriminant function is a Euclidean Distance; and iteratively calculating a neighborhood radius associated with the BMU using a neighborhood kernel (function) to determine neighboring network nodes for updating, and updating values of synoptic weights for neighboring network nodes within the calculated neighborhood radius for a fixed number of iterations.

The controller can generate an output value of the SOM network based upon input attributes for the clinical patient event, wherein the output value is a graphical display showing a particular category for the patient event.

In both first and second embodiments, the controller can conduct post-processing of the output value, which can include denormalization.

It should be noted that all or some of the aspects of the first and second embodiments can be combined.

BRIEF DESCRIPTION OF THE DRAWINGS

The accompanying figures, in which like reference numerals refer to identical or functionally similar elements, together with the detailed description below are incorporated in and form part of the specification and serve to further illustrate various exemplary embodiments and explain various principles and advantages in accordance with the present invention.

FIG. 11B is an illustration of an exemplary data set for patient input attributes for various patient events.

DETAILED DESCRIPTION

In overview, the present disclosure concerns a system which includes a Data Collection Engine (DCE), backend devices such as one or more server devices and a throughput management device (TMD), and a plurality of client devices.

The instant disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions.

It is noted that some embodiments may include a plurality of processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1:
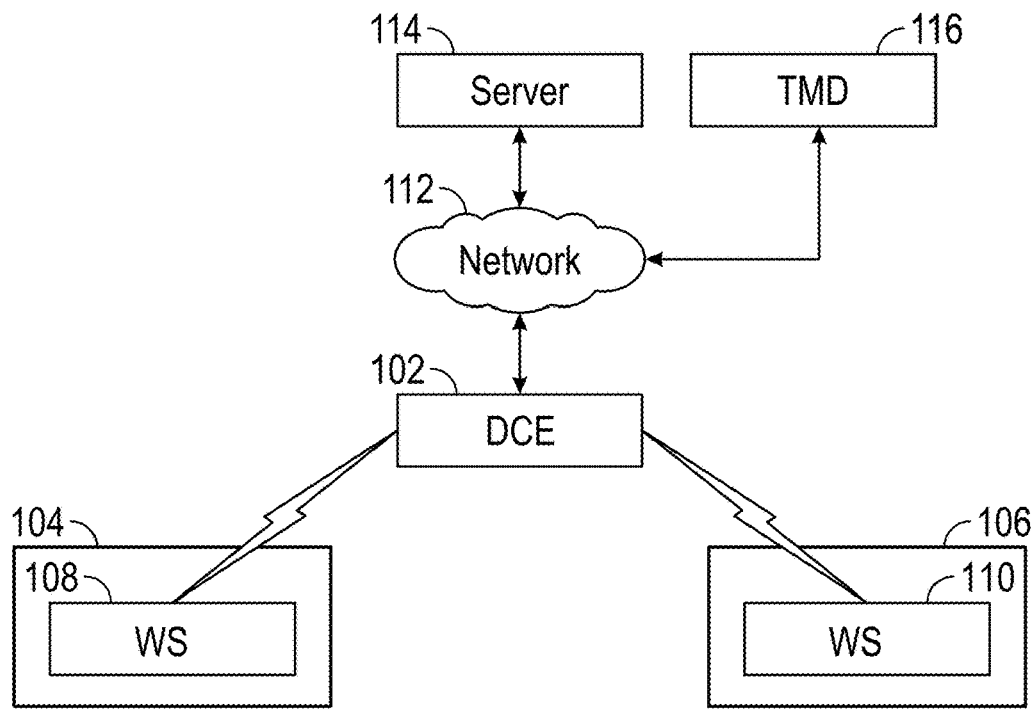
FIG. 1 illustrates an exemplary core operating environment in which a Data Collection Engine (DCE) receives patient attributes associated with an event and transmits the data to a server via a connection to a network.

Referring to FIG. 1, an exemplary operating environment in which the system according to various embodiments can be implemented will be discussed. The environment includes a DCE 102 communicating with first and second data sources 108, 110 which can be disposed in separate first and second rooms 104, 106. The first and second rooms 104, 106 can be, for example, separate rooms of a hospital facility for performing computed tomography (CT) scanning. Each of the data sources 108, 110 can be, for example, work stations storing DICOM images of imaging studies, patient information, etc.

As discussed more fully below, the communication between the data sources 108, 110 and the DCE 102 is preferably wireless; however, wireline communication or a combination of wireless and wireline communication can also be used in some cases. The DCE 102, although shown here as a single entity, can include sub-portions in each of the rooms 104, 106. Moreover, as discussed later, the system likely includes many DCEs (see FIG. 6). The DCE 102 communicates with one or more server devices (represented generally by and referred to hereon as "server") 114 via a connection to a network 112 such as a local area network (LAN), wide area network (WAN), the Internet, etc. A TMD 116 can communicate with the server 114 and the DCE 102 via a connection to the network 112. The communication between the DCE 102 and the data sources 108, 110, between the DCE 102 and the server 114 or TMD 116, and/or between the server 114 and the TMD 116 can be encrypted or unencrypted. The network 112 can be, for example, a private LAN for the hospital facility. The server 114 can be a computing device local to the hospital facility. On the other hand, the network 112 can be the Internet, the DCE 102 can be local to the hospital facility and the server 114 can be one or more remote computing devices. One of ordinary skill in the art should appreciate that the server 114 can represent entities necessary for providing cloud computing such as infrastructure and service providers.

Figure 2:
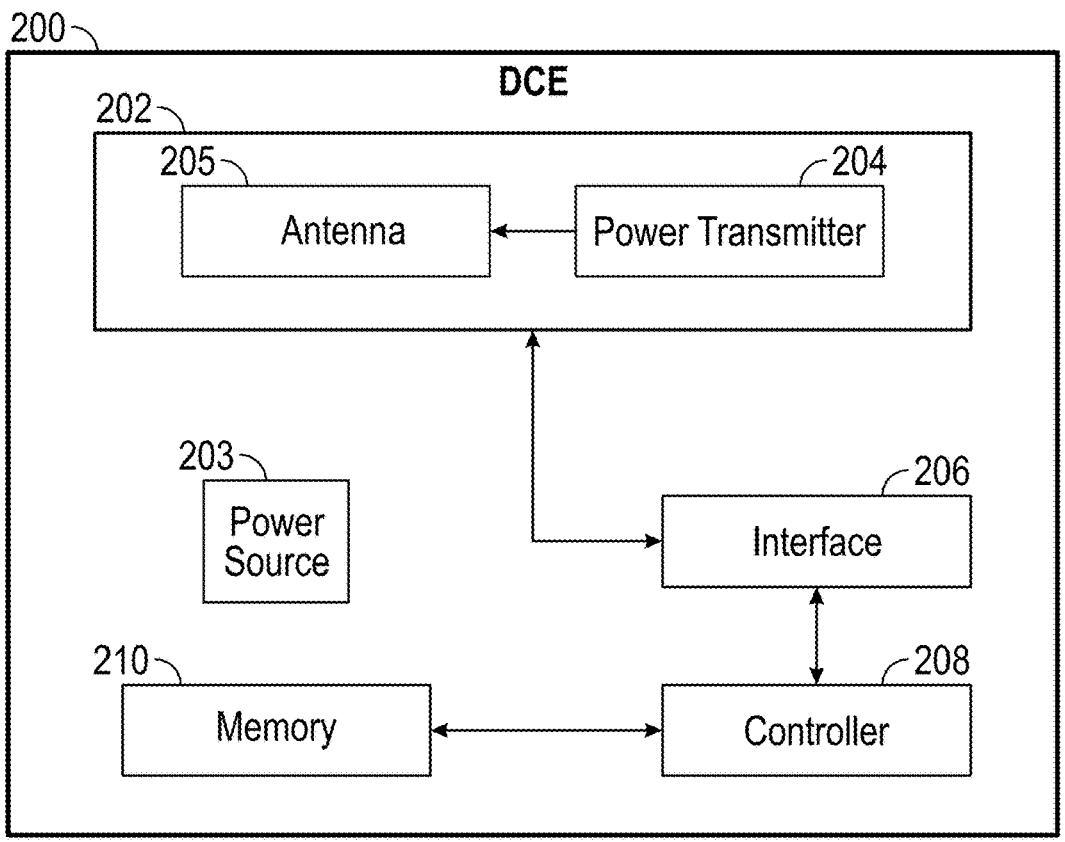
FIG. 2 is a block diagram illustrating exemplary portions of the DCE.

Referring to the block diagram of FIG. 2, portions of an exemplary DCE 200 will be discussed. The DCE 200 includes a transceiver 202, a power source 203, an interface 206, a controller 208 and one or more memory portions depicted by memory 210.

Referencing the Open Systems Interconnection reference model (OSI model), the transceiver 202 can provide the physical layer functions such as modulating packet bits into electromagnetic waves to be transmitted and demodulating received waves into packet bits to be processed by higher layers (at interface 206). The transceiver 202 can include an antenna portion 205, and radio technology circuitry such as, for example, ZigBee, Bluetooth and WiFi, as well as an Ethernet and a USB connection. The transceiver 202 also includes a wireless power transmitter 204 for generating a magnetic field or non-radiative field for providing energy transfer from the power source 203 and transmitting the energy to, for example, an RFID tag by antenna portion 205. The power transmitter 204 can include, for example, a power transmission coil. The antenna portion 205 can be, for example, a loop antenna which includes a ferrite core, capacitively loaded wire loops, multi-turn coils, etc. In addition to energy transfer, the transceiver portion 202 can also exchange data with the RFID tag. Data transmission can be done at, for example, 1.56 MHz. The data can be encoded according to, for example, Amplitude Shift Keying (ASK). The transceiver 202 includes a power transmission system composed of the antenna 205 and the power transmitter 204.

The interface 206 can provide the data link layer and network layer functions such as formatting packet bits to an appropriate format for transmission or received packet bits into an appropriate format for processing by the controller 208. For example, the interface 206 can be configured to encode or decode according to ASK. Further, the interface 206 can be configured in accordance with the 802.11 media access control (MAC) protocol and the TCP/IP protocol for data exchange with the server via a connection to the network. According to the MAC protocol, packet bits are encapsulated into frames for transmission and the encapsulation is removed from received frames. According to the TCP/IP protocol, error control is introduced and addressing is employed to ensure end-to-end delivery. Although shown separately here for simplicity, it should be noted that the interface 206 and the transceiver 202 may be implemented by a network interface consisting of a few integrated circuits.

The memory 210 can be a combination of a variety of types of memory such as random access memory (RAM), read only memory (ROM), flash memory, dynamic RAM (DRAM) or the like. The memory 210 can store location information and instructions for configuring the controller 208 to execute processes such as generating messages representative and indicative of patient events received from data sources as discussed more fully below.

The controller 208 can be a general purpose central processing unit (CPU) or an application specific integrated circuit (ASIC). For example, the controller 208 can be implemented by a 32 bit microcontroller. The controller 208 and the memory 210 can be part of a core (not shown).

Figure 3:
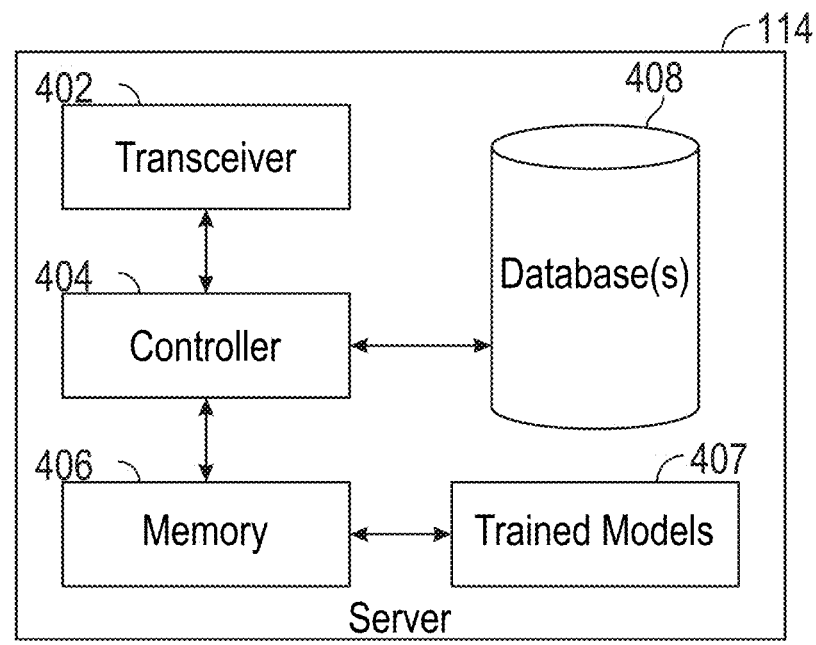
FIG. 3 is a block diagram illustrating exemplary portions of a server device.

Referring to FIG. 3, the server 114 includes a transceiver 402, a controller 404, a first memory portion 406, a second memory portion 407 and one or more databases stored in another memory source depicted generally by 408. The transceiver 402 can be similar to the transceiver of the DCE. The transceiver 402 receives medical data via the network from the DCE, data retrieval requests from the TMD 116 and sends replies to the data retrieval requests.

The memory portions 406, 407, 408 can be one or a combination of a variety of types of memory such as RAM, ROM, flash memory, DRAM or the like. The memory portion 406 includes instructions for configuring the controller 404. The second memory portion 407 includes one or more trained models. It should be noted that the database and the trained models can be included in the memory portion 406. They are shown separately here in order to facilitate discussion.

The database 408 can include: patient identifications, attributes associated with each patient identification such as dispositions, scheduled surgeries, location history, consumed medical items, imaging studies, etc.; patient events including a plurality of input attributes and a quantifiable outcome for each patient event; and medical professional identifications, attributes associated with each medical professional such as scheduled surgeries, location history, consumed medical items, etc.

The controller 404 is configured according to the instructions in the first memory portion 406 to determine data in the database 408 that is associated with the patient identifications (received in the message from the DCE); store data in the message from the DCE in the database 408 to be associated with the patient identification; and as will be discussed more fully below, predict an outcome associated with a clinical patient event based upon input attributes of the clinical patient event into a trained model such as a neural network model or self-organizing map network.

Figure 4:
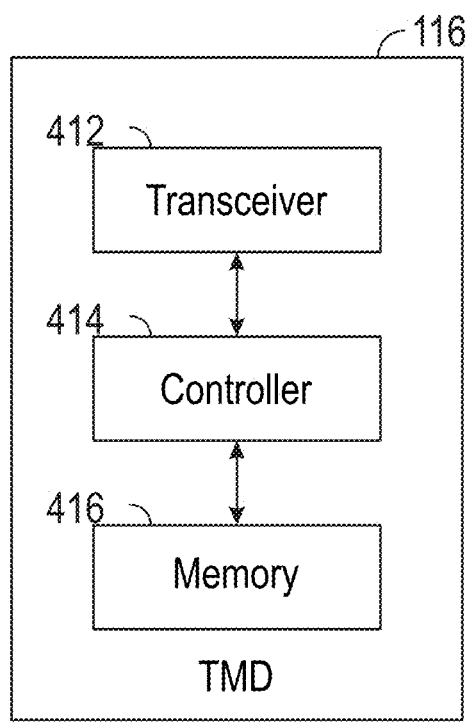
FIG. 4 is a block diagram illustrating exemplary portions of a TMD.

Referring to FIG. 4, the TMD 116 includes a transceiver 412, a controller 414 and memory 416. The transceiver 412 can be similar to the transceiver of the DCE. The transceiver 412 receives information or resource requests such as, for example, http requests, via the network, from the client devices and other medical data storage sources. The resource request can include verification credentials such as a token issued from a certification authority (which must be determined to be valid and to contain the requisite claims for the resource being requested in order for the request to be successfully processed), and a user identifier and an information request for calculated quantifiable outcomes for a plurality of patient transactions. The transceiver 412 sends an information reply to the client device. The controller 414 is configured according to instructions in the memory 416 to generate either solely visualization data (i.e. a json object) or graphical displays (i.e. html markup and javascript) including visualization data retrieved from server 114 as the information reply that can then be used to generate a display on the client device.

In the discussion here, the server 114 and TMD 116 are shown as separate entities for ease of discussion. However, in actual implementation the server 114 and TMD 116 may be implemented within a single computing device. Moreover, the portions of server 114 may be distributed among various computing devices. For example, the trained models shown stored in memory portion 407 or the database(s) 408 could be stored at a plurality of different computing devices.

Figure 5:
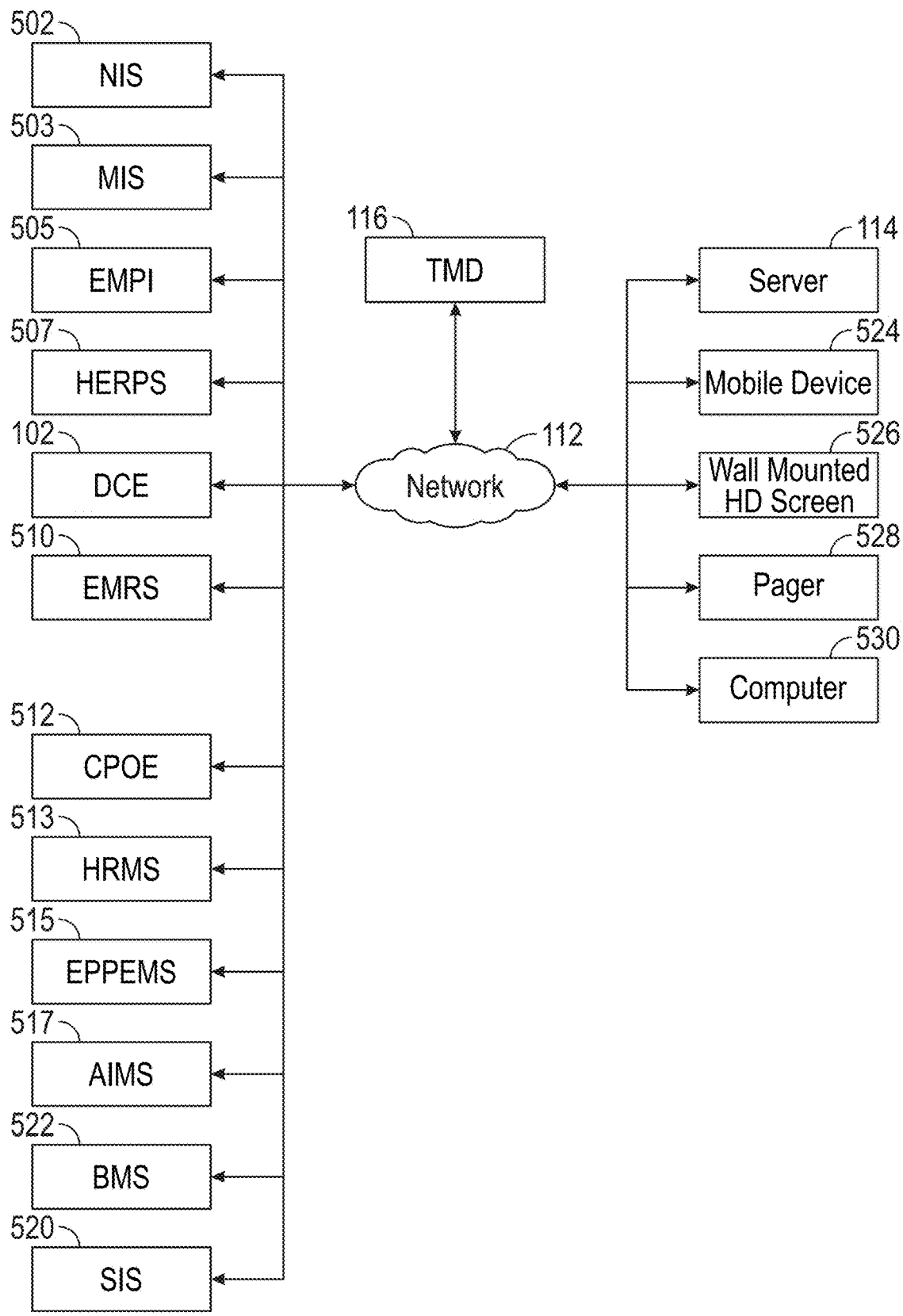
FIG. 5 illustrates an exemplary expanded operating environment in which the server device receives medical data from various medical data sources.

Referring to FIG. 5, an expanded exemplary operating environment is shown to illustrate how the backend devices (server 114 and TMD 116) communicate with various medical data storage sources such as Nursing Information System (NIS) 502, Pharmacy Management Information System (MIS) 504, Hospital Enterprise Master Patient Index (EMPI) 506, Hospital Enterprise Resource Planning System (HERPS) 508, Electronic Medical Records System (EMRS) 510, Hospital Computerized Provider Order Entry (CPOE) system 512, Human Resources Management System (HRMS) 514, Employee Performance Planning and Evaluation Management System (EPPEMS) 516, Anesthesiology Information Management System (AIMS) 518, Perioperative Anesthesia System/Surgical Information System (SIS) 520, Hospital Bed Management System (BMS) 522 and client devices such as mobile device 524, wall mounted HD screen 526, pager 528 and a computer 530 via the network 112.

The server 114 and TMD 116 can be considered the backend devices of the system. The client devices of the system can be a desktop or fixed device, a mobile device, or another system (i.e. another backend server) that can run a native application or an application in a web browser. The various client devices contain a controller that executes instructions and a transceiver. The client devices can communicate with the backend system over the network 116 using a remote procedure call (RPC) or via Representational State Transfer (REST)-like or REST-ful architectural style or a messaging based architecture (i.e. like Health Level 7). The client devices communicate with the backend devices over Hypertext Transfer Protocol (HTTP), over another networking protocol encapsulated in Transmission Control Protocol (TCP), via message queues (for example Microsoft Message Queuing, Rabbit MQ, etc.) or any other protocols, for example, User Datagram Protocol, etc. The devices may also communicate via a cellular network (GSM, GPRS, CDMA, EV-DO, EDGE, UMTS, DECT, IS-136/TDMA, iDEN AMPS, etc.) or via other network types (i.e. Satellite phones). The data exchanged between the client devices and the backend device(s) can optionally be encrypted using Secure Sockets Layer (SSL), Transport Layer Security (TLS) and decrypted on the client device(s) and the backend device(s). The data may also be encrypted in transit using methods other than SSL/TLS (for example using a keyed-hash message authentication code in combination with a secret cryptographic key) and can be decrypted by the client or backend devices. SSL/TLS can alternatively be used in conjunction with one of the alternative encryption methodologies (belt-and-suspenders). Also, as mentioned, a client device may also consist of another third party back end system, such as another server that communicates with a database server.

Creating and Storing Patient Imaging Studies

Returning to FIG. 1, the DCE 102 can collect data from work stations 108, 110. The data can be computed tomography (CT) scan images. The process for generating and storing the CT scan images will be discussed here.

X-Ray Generation (in an x-Ray Tube)—Process Occurs Inside of an Evacuated Glass Envelope (in a Vacuum)

1. Charge cathode (positively charged cathode)—generally consists of a tungsten spiral.
2. Charge anode (negatively charged anode).
3. Pass electrical current through cathode causing tungsten spiral to heat up and emit (therm ionic emission) electrons (electron acceleration caused by passing a high voltage).
4. Potential difference between anode and cathode (tube charge, expressed in kilovolts (kV)) will cause electrons to shoot towards positively charged anode (focus/target).
5. At the anode the electron flow (tube current, expressed in milliamperes (mA)) deaccelerates (by the nuclei of the target material or by collision of projectile electrons with electrons in the target atoms) and the kinetic energy of the electrons is converted to electromagnetic radiations called x-rays (a beam of light with a very small wavelength—smaller than UV and invisible to the eye) and heat (in fact, most of the electron energy is converted to heat, thus many of the design features of x-ray tubes are for the dissipation of large quantities of heat).
6. X-rays are emitted from the x-ray tube.

X-Ray Image

1. X-ray beam leaves the x-ray tube and passes through the patient (when x-rays travel through the body they are absorbed by the tissue and bone (different kinds of atoms); the harder the tissue (the bigger the atom) the more is absorbed.
2. Any x-ray radiation that makes it through the patient's body hits a phosphorous plate/detector.
3. The whiteness (density) depends on the amount of x-ray radiation passing through the tissue.
4. The more x-rays are obstructed (absorption or dispersion) the lower the magnitude of the radiation that arrives at the phosphorous plate/detector and the denser (whiter) the image.

Scan

1. Patient is placed on a table
2. Table with patient on it is moved horizontally through a gantry with a circular shaped opening in the center; the gantry is generally positioned upright and is often perpendicular to the table, though the gantry can have a tilt or angle and a helical CT will have a pitch (due to the method of image acquisition)
3. An x-ray tube is positioned on one side of the circular shaped opening in the gantry and an arc of multiple detectors are positioned directly opposite the x-ray tube; this arrangement allows x-rays emitted from the x-ray tube to pass through the patient and then to the detectors (detector array)—note there are several variations of this arrangement depending on the "generation" of the CT Scanner.
4. The x-ray tube and detectors are kept in this fixed relative position and together rotate around the circular opening in the gantry (and the patient on the table) and an x-ray beam (x-ray tube is collimated to a wide x-ray beam that is fan-shaped, a so called "fanbeam," which covers the entire patient) is periodically passed through the patient (pulsed) in a thin axial slice (multiple axial slices can be obtained in each rotation in CT scanners that do multi-slice scanning) from multiple angles (i.e. simplistic way to think about it would be from top to bottom, from left to right, from bottom up, from right to left, and so on and so forth) and is directed toward an arc shaped row of detectors (detector array, usually more than 800 in 3rd generation CT scanners) which measure the radiation transmission through the patient; alternatively rather than pulsing the x-ray beam, the detectors can be sampled at a very high rate while the x-ray field is emitted (i.e. constantly emitted or some variation thereon), achieving the same end result; depending on the generation of the CT scanner there are some variations of this process, but ultimately thin slices of x-ray beams, which are fan-shaped in 3rd generation and may of the higher "generation" scanners (3rd generation fan beam geometry has the x-ray tube as the apex of the fan; 4th generation has the individual detector as the apex of the fan), are passed from an x-ray tube through the patient and the average linear attenuation coefficient is measured by an arc which contains an array of detectors that are directly opposite the x-ray tube emitting the x-rays; this process is repeated resulting in the acquisition of multiple projections taken from different directions.
5. The detectors measure the average linear attenuation coefficient mu (μ) between the tube and detectors; the attenuation coefficient reflects the degree to which the x-ray intensity is reduced by a material; density at a given point on an image represents the x-ray attenuation properties within the patient along a line between the x-ray focal spot and the point on the detector corresponding to the point on the image.
6. Common detectors used in CT scanners are scintillator-photodiode solid state detectors. Materials used as scintillators include caesium iodide (CsI), cadmium tungstate ($CdWO_4$) or ceramic materials based on yttrium-gadolinium oxides); x-rays interact with the scintillator and produce visible light; the visible light is converted to an electronic current by the photo diode.
7. Signal from detectors goes to amplifiers for signal magnification and then is sent to sample/hold unit
8. Sample/hold unit (S/H) performs sampling and assigns shades of gray to the pixels in the digital matrix corresponding to the structures.

9. Analog-to-digital converter (ADC) converts analog signal output from the scanning equipment to a digital signal (so it can be processed by a computer).
10. Data is transmitted to computer workstation for the CT scanner.
11. Software on computer workstation for CT scanner calculates and analyzes data from each detector in each level and reconstructs multiple, two dimensional cross sectional images.
12. To explain the measurement process, focus on just one 'pencil-beam' of x-rays (a fan-beam can be considered to be made up of many adjacent pencil-beams). The beam of x-rays is translated across and rotated about the patient; attenuation measurements from multiple pencil beams at a given angle is termed a projection; each pencil-beam measurement is termed a raysum (a measurement made by a CT detector is proportional to the sum of the attenuation coefficients that lie along the ray defined by the pencil-beam of x-rays).
13. Assuming the x-ray beam is monoenergetic, the intensity of an x-ray beam, I, of incident intensity $I_0$ transmitted through a small volume of tissue having a thickness x and attenuation coefficient µ1 is:

$$I_1 = I_0 \exp(-\mu_1 x)$$

As an x-ray beam traverses from one side of the patient to the other, the x-ray beam is attenuated by all of the voxels through which it passes (a voxel is one volume element from the square matrix the patient [and image] are sectioned into—called a pixel on the image); thus, the emerging x-ray beam will have an intensity I given by:

$$I = I_0 \exp\left(-x \sum_{i=1}^{n} \mu_i\right);$$

which can be rearranged to:

$$\ln \frac{I_0}{I} = x \sum_{i=1}^{n} \mu_i$$

Therefore, the natural logarithm of the ratio of incident x-rays to transmitted x-rays is proportional to the sum of the attenuation coefficients of the voxels in the path of the beam.

The x-rays produced by an x-ray tube are polyenergetic (causes beam hardening which causes an underestimation of the pixel values in an image), so this provides an estimate. Several algorithms are used to correct for beam hardening; they are used to modify the raysums prior to reconstruction.

A CT image consisting of 512 rows each containing 512 pixels (i.e. a 512×512 matrix), would essentially be a square matrix with a total of 262,144 pixels; the image reconstruction process calculates a value for the linear attenuation coefficient for each of the 262,144 voxels corresponding to these pixels.

The image can be reconstructed using any variety of methods for example, Fourier (projection slice theorem) transform based filtered backprojection; another approach that can be employed is iterative reconstruction, backprojection summation, convolution backprojection or others. Reconstruction is the mathematical process of converting sinograms into 2D slice images. During reconstruction, raw intensity data in the sinogram are converted to CT numbers.

A 12-bit scale allows for 4096 potential values and is commonly used in medical systems; a 16 bit scale allows for 65535 potential values.

14. Each 2D CT image is represented as the Matrix of the value of the image at each location; each square in a matrix is called a pixel (also known as a picture element); each element or number in the image matrix represents a three dimensional volume element in the imaged cross sectional area called a voxel; each pixel has a number which represents the x-ray attenuation in the corresponding voxel of the imaged object; CT pixel size is determined by dividing the field of view (FOV)—determines how much anatomy is scanned—by the matrix size which is generally 512×512. For example, if the FOV is 40 cm or 400 mm and the Matrix is 512×512, then the pixel size is 400/500=0.78 mm.
15. Each 2D CT image corresponds to a 3D section of a patient (matrix dimensions×slice thickness).
16. CT slice thickness is thin (1-10 mm usually) and is approximately uniform.
17. The 2D array of pixels in the CT image corresponds to an equal number of 3D voxels (volume elements) in the patient.
18. Each pixel on the CT image displays the average x-ray attenuation properties of the tissue in the corresponding voxel.
19. Mu values are scaled to that of water to give the "CT Number" (Hounsfield units): CT number=$((mu_{tissue} - mu_{water})/mu_{water}) \times 1000$, a relative comparison of the attenuation of a voxel of tissue to an equal volume of water.

Storing CT Scans
1. Once acquired and reconstructed, CT scans are often persisted (archival) in some storage medium for future access. Not uncommonly, a standardized image storage format is utilized, such as the Digital Imaging and Communications in Medicine (DICOM) standard, which was created by the National Electrical Manufacturers Association (NEMA). The specifics of the DICOM standard are maintained by NEMA (nema.org) at (ftp://medical.nema.org/medical/dicom) and are incorporated herein by reference.
2. Each DICOM file contains a header which includes meta-data about the patient and the scan and the actual image data. DICOM image data can be persisted uncompressed or compressed to reduce the size of the file. The meta-data in the header is organized with a standard set of "tags" which also serve to group related data elements. After the header in a DICOM file, the pixel intensity data is available, typically indexed or tagged by the attribute (7FE0) consistent with the DICOM standard, and consists of a data stream of the pixel samples that comprise the image (typically stored as bytes which, again may be compressed or uncompressed). Often the pixel intensity data is transformed from the in memory representation to a representation that is best for persistence on the storage medium. For example, a CT scan's pixels, which have intensity measured in Hounsfield units (which can have negative values), often has its pixel intensity values stored on disk as unsigned integers. There are other reasons as well for doing such a linear transformation for persistence, including optimizations that make storing the values use the fewest bits possible. Different manufacturers may have different methodologies. Two properties in the header of each DICOM image file store information about this linear transformation: (0028|1052) Rescale Intercept and (0028|1053) Rescale Slope. The in memory representation of the CT Number (Hounsfield Units) can be derived from the persisted pixel intensity value using the following methodology: U=m×SV+b, where U is the CT Number, m is the rescale slope, b is the rescale intercept and SV is the persisted or stored value. As such, the persisted data for a CT scan, not uncommonly, has a negative intercept to arrive at an unsigned integer for persistence. Because the values in a medical imaging study can potentially vary greatly from slice to slice, the rescale intercept and slope values can vary and is a property that is stored and available for each slice of a CT Scan study. There are other properties in the header that also describe the stored value including: (0028|0100) Bits Allocated, (0028|0101) Bits Stored, (0028|0103) Pixel Representation, (0028|0002) Samples per Pixel, among others.

Reading in CT Scans

The DCE (or one of the backend devices) can read in CT Scans which have been persisted on storage medium in a variety of formats. One exemplary case is CT Scans stored in the DICOM format. A given CT scan typically consists of multiple DICOM files, one for each "slice" of the study. The system reads the DICOM files associated with a given study from the specified location and storage medium which is configurable. Once in memory, the array of pixel intensity data included in the DICOM files can be read into an array in memory. The rescale intercept and the rescale slope for each slice can also be read from the header information in the DICOM files and put into memory. Using the previously described methodology (U=m×SV+b, where U is the CT Number, m is the rescale slope, b is the rescale intercept and SV is the persisted or stored value), the intensity data (SV) for each pixel, the rescale slope (m), and the rescale intercept (b) . . . the CT Number (U) can then be derived/calculated; this value will then be in Hounsfield Units.

The system can ingest large multidimensional arrays of CT Scan data with intensities in Hounsfield Units as the starting point for pre-processing. This data often is initially derived from some data store where CT scans are persisted.

The example shows this process implemented in the Python programming language. One function described reads in a patient's CT Scan located at a specified path passed into the function using the Python library Pydicom; this function also determines the slice thickness and persists this data conveniently in memory for future use using NumPy a library for the Python programming language which provides support for scientific computing involving large, multi-dimensional arrays and matrices, including high-level mathematical functions to operate on these arrays.

Sample Python Code for loading a CT Scan from a data store and determining and persisting in memory the slice thickness

```
def loadCtScan(path):
    print('starting loadCtScan')
    slices=[pydicom.read_file(path+'/'+study) for study in
        os.listdir(path)]
    slices.sort(key=lambda x: float(x.ImagePositionPatient
        [2]))
    try:
        sliceThickness=numpy.abs(slices[0]. ImagePosi-
            tionPatient[2]-slices[1].ImagePositionPatient[2])
    except:
        sliceThickness=numpy.abs(slices[0].SliceLocation-
            slices[1].SliceLocation)
    for imgSlice in slices:
        imgSlice.SliceThickness=sliceThickness
    print('completing loadCtScan')
    return slices
```

Another function takes an array of "slices" passed into the function and returns an array of the CT Scan slices with the intensity values for each pixel in each slice converted (transformed) to Hounsfield Units derived from the stored value loaded into memory from the DICOM file. This function also uses NumPy to carry out mathematical operations on these large multi-dimensional arrays of data which permits the use of very tersely written code.

Sample Python Code for transforming pixel intensity values from the value stored in memory in a DICOM file to a CT number (in Hounsfield Units) using the Rescale Intercept and the Rescale Slope from the DICOM file header in each "slice" of the passed in CT Scan slices

```
def getHounsfieldUnits(slices):
    print('starting getHounsfieldUnits')
    img=numpy.stack(imgSlice.pixel_array for imgSlice in
        slices)
    img=img.astype(numpy.int16)
    for sliceNumber in range(len(slices)):
        intercept=slices[sliceNumber]. RescaleIntercept
        slope=slices[sliceNumber]. RescaleSlope
        if slope !=-1:
            img[sliceNumber]=slope     img[sliceNumber].
                astype(numpy.float64)
            img[sliceNumber]=img[sliceNumber].astype
                (numpy.int16)
        img[sliceNumber]=img[sliceNumber]+numpy.int16
            (intercept)
    print('completing getHounsfieldUnits')
    data=numpy.array(img, dtype=numpy.int16)
    return data
```

Values in Parts of the Body

The Hounsfield scale applies to medical-grade CT scans but not to cone beam computed tomography (CBCT) scans.

Unclotted Blood has an HU of +13 to +50. Clotted Blood has an HU of +50 to +75. Blood for a Subdural hematoma in first hours has an HU of +75 to +100. Blood for a Subdural hematoma after three days has an HU of +65 to +85. Blood for a Subdural hematoma after 10-14 days has an HU of +35 to +40.

CT of the Head

Figure 11A:
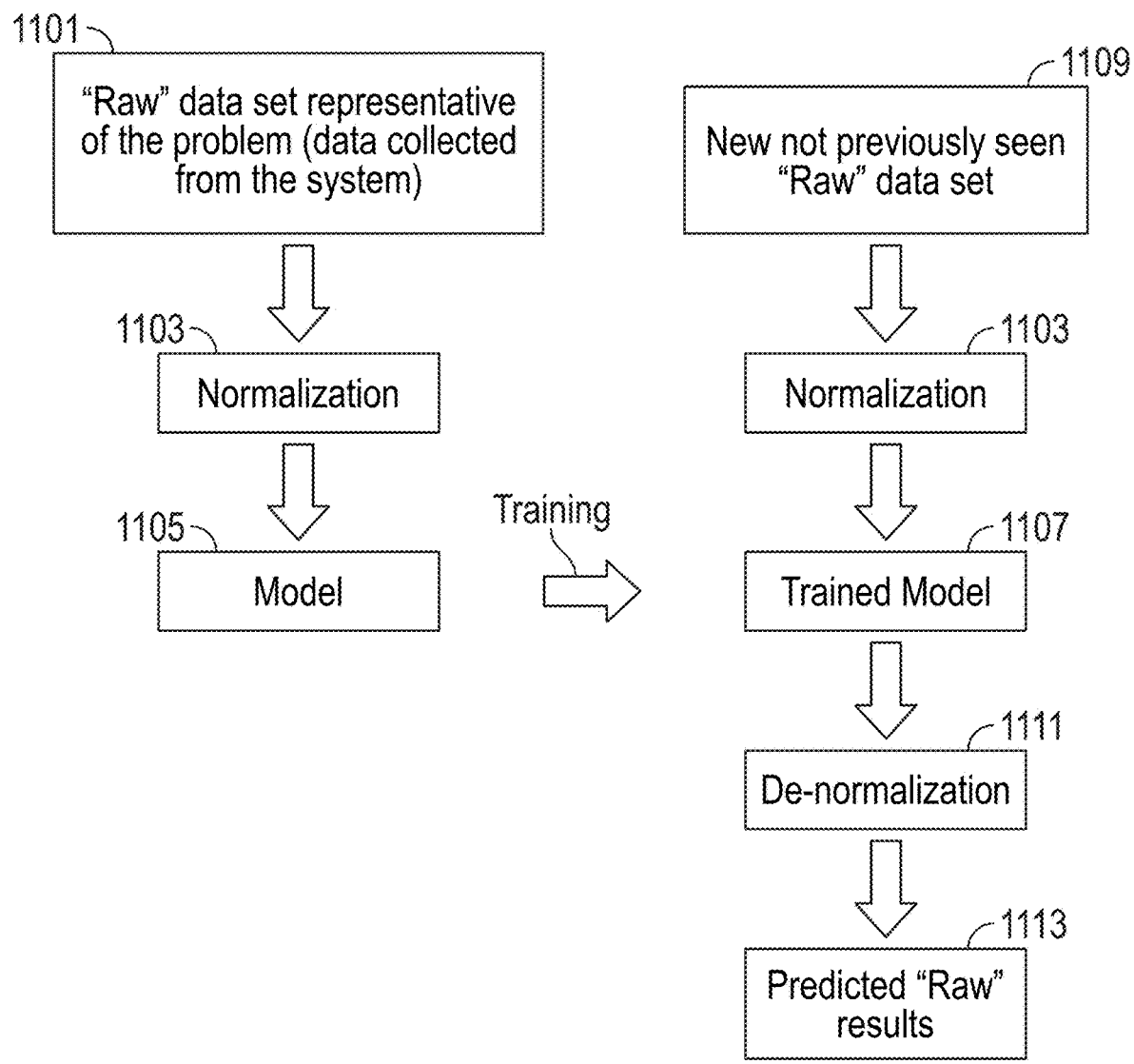
FIG. 11A is a block diagram illustrating high level operations for creating a trained neural network model (NNM) according to an embodiment.

CT scanning of the head uses a series of x-rays of the head taken from many different directions. Typically used for quickly viewing brain injuries, CT scanning uses a computer program that performs a numerical integral calculation (the inverse Radon transform) on the measured x-ray series to estimate how much of an x-ray beam is absorbed in a small volume of the brain. Typically, the information is presented as a series of cross sections of the brain Creating a Trained Neural Network Model to Predict an Outcome The server device 114 stores a trained neural network model which is used to predict an outcome of a clinical patient event. A representation of the process for creating, training and using the trained model is shown in FIG. 11A. Raw data 1101 is normalized 1103, and then input into the model 1105. The model 1105 is trained to form the trained model 1109 is normalized 1103 and input into the trained model 1107. The output data of the trained model 1107 is de-normalized 1111 to obtain the output data (predicted raw results) 1113. As shown in FIG. 11B, the raw data 1101 and new data 1109 include sets of data [1, 2 ... N] with known outcomes and properties of each of the data. For example, the data can be past patient events with known outcomes (whether or not surgical intervention was required). The properties of the data can be imaging studies or other patient attributes. Moreover, the output of at 1107 or 1113 in some cases may become the input at 1105 or 1103, respectively; in other words, the output or prediction of one trained model, may become the input of another trained model.

The model 1105 is trained by an iterative machine learning algorithm. After initial deployment, the server 114 will also continuously collect data from a variety of sources along with actual related healthcare system clinical and operational outcomes; this data can subsequently be used as training data. As such, the server is able to continuously learn and improve its ability to predict the outcomes of interest. In addition, the knowledge of the system can continue to evolve in the event the system dynamics change. There is a relationship between the multitude of attribute data the system collects about an event and the outcome in question. Exemplary attributes the server 114 collects about an event that can be used include: the patient's age, the patient's laboratory results, the patients diagnostic imaging results, the patient's vital signs, to provide several examples. However, there is no one specific mathematical relationship or equation that describes the relationship between these exemplary attributes of the patient event and the outcome. However, because of the server's machine learning capabilities it has the ability to "learn" or be trained from pre-existing data and from the data it collects prospectively. Said another way, the server 114 "learns" from experience.

Data Set Encoding, Normalization and De-Normalization

Neural network models only use numerical double values for training and processing. Thus, any nominal categorical data fields that are a part of raw data that will ultimately be used by models in the system are first encoded to numerical values and "raw" numerical data in many cases by a preprocessing such as normalization 1103 before training and processing. While normalization and de-normalization steps may not be explicitly described as being carried out before or after data consumption by any given model, this should not be misconstrued and lead to the assumption that these routine steps are not carried out.

The normalization processes 1103 and corresponding de-normalization processes 1111 are used not only for training data sets, but also for new, unseen data that is fed into the trained models. Though it is not the rule, frequently, the output from the trained models is normalized and in the event it is a categorical data field the output will also be encoded. Thus, often output from the system models has to be de-normalized and possibly decoded to yield the "raw data," "human readable" format of the predicted output.

Neural network training is often more efficient when independent numeric data (x-data) is normalized. For this reason, the system most often normalizes numeric data along the same scale being utilized by the model for all data fields, including nominal data fields. The scale the system utilizes for normalization depends on the particular activation function employed by a given model. In most cases this results in normalization either from −1 to 1 or 0 to 1, however, in some cases intermediate range values may be used as well, such as −0.5 to 0.5, for example. This "raw data" normalization step also prevents predictors or inputs that are relatively larger in magnitude (as compared to other predictors or inputs) from having more relative influence on the change in the value of synaptic weights during training of the system models. For problems with normalized nominal data, one neuron is required to represent each numeric data field type.

Figure 12A:
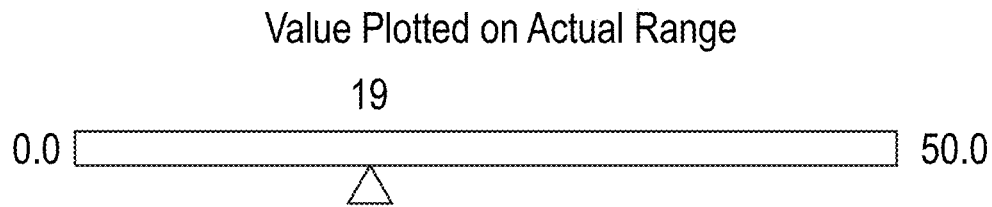
FIG. 12A-12B are illustrations of various exemplary approaches for normalizing the data set.

An example of one of the independent predictors (input x-data) or input attributes that can be utilized by the system is the number of medications a given patient. Suppose a patient has 19 discharge medications and that this "raw data" value needs to be normalized to a −1 to 1 normalization range. If the actual range of the possible number of discharge medications is 0 to 50, for example, then to normalize this input x-data, the system's continuous or numeric normalization process would carry out normalization calculations similar to those illustrated herein. Initially, the value can be plotted on an actual range as shown in FIG. 12A. Then a normalization calculation can be carried out as shown below:

$$\{[(19-0.0)*(1.0-(-1.0))]/(50.0-0.0)\}+(-1.0)=-0.24$$

Figure 12B:
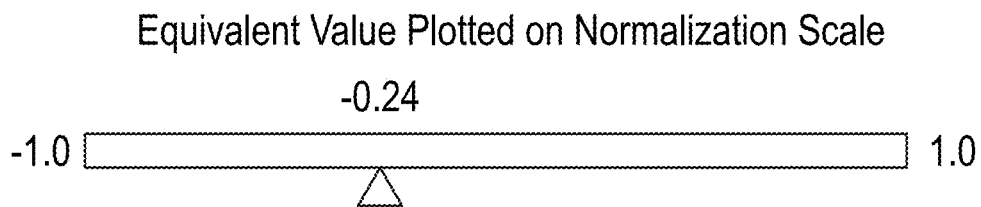

Referring to FIG. 12B, equivalent value plotted on a normalization scale is shown.

Figure 13A:
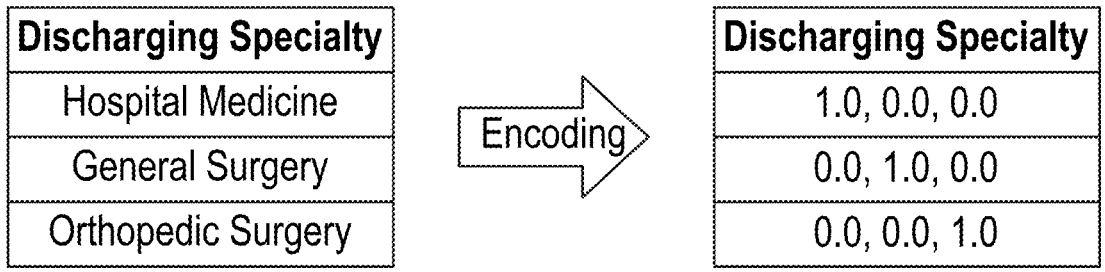
FIG. 13A-13B are illustrations of various exemplary approaches for encoding the normalized data set.

In the encoding process, the system may encode classification labels into double values within the normalization range such as −1 to 1 or 0 to 1. The scale the system utilizes for encoding depends on the particular activation function employed by a given model. An approach the system employs at times to encode nominal data fields is so called one-of-N encoding as shown in FIG. 13A. For example, one of the attributes that may be used is the discharging medical or surgical specialty. In this case the hospital has three medical and surgical specialties that discharge patients: hospital medicine, general surgery and orthopedic surgery. The nominal categories are represented by double values within a normalization range of 0 to 1. Another variety of this approach that can be used is one-of-C-dummy encoding. When this method is employed, the number of neurons needed to represent a given number of nominal data field types is equal to the number of distinct nominal categories. However, one-of-N encoding is subject to an unequal distribution of error (unequal fault behavior) for wrong predictions which can occur when there are more than two nominal categories. For example, if the value predicted by a given model is orthopedics {0.0, 0.0, 1.0} but the ideal (real) value is actually general surgery {0.0, 1.0, 0.0}, it is apparent that there is only error in two parts. Said another way, if the predicted and the ideal (real) values are compared, the first value is 0.0 in both (i.e. is correct), while the other two values are both wrong. This is unequal distribution of errors.

Figure 13B:
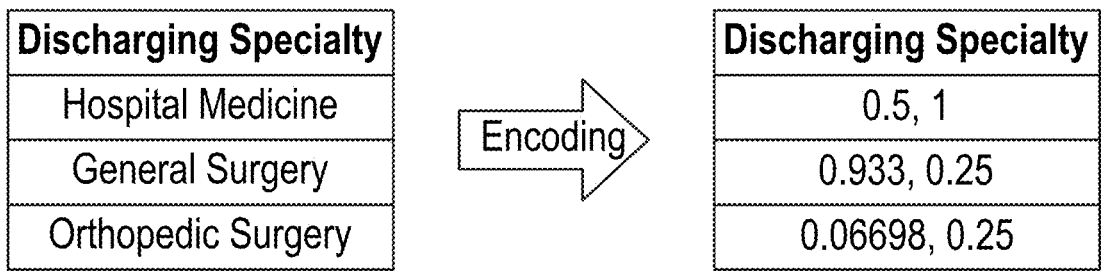

Due to this shortcoming of one-of-N encoding, particularly in instances when there are more than two nominal categories, the server can employ equilateral encoding (one-of-(N-1) encoding shown in FIG. 13B or one-of-(C-1) dummy encoding for encoding nominal categorical data. When equilateral encoding is used fault behavior is equally distributed when wrong predictions are encountered. The equilateral encoding used by the system is based on the Euclidean normalization technique which results in each nominal category having equal Euclidean distances from the others. The Euclidean Distance is calculated as shown below:

$$\text{distance} = \sqrt{\frac{(i_1 - a_1)^2 + (i_2 - a_2)^2 + \ldots + (i_n - a_n)^2}{n}}$$

Where the variables represent the following:
i=ideal (real) output value
a=actual (predicted) output value
n=number of sets of ideal and actual values With equilateral encoding, all classes are able to be represented by a number of doubles equal to one minus the total number of nominal data classes, in this case 2 (3−1=2). When this technique is used, every set of possible ideal and actual combinations in the above example will result in an equivalent Euclidean distance.

Ideal: {0.5, 1} Actual: {0.933, 0.25}
Euclidean Distance:
$=((0.5-0.933)^2+(1.0-0.25)^2)^{1/2}$
$=(-0.433^2+0.75^2)^{1/2}$
$=(0.187489+0.5625)^{1/2}$
$=(0.749989)^{1/2}$
$=0.8660$ Ideal: {0.06698, 0.25}
Actual: {0.5, 1}
Euclidean Distance:
$=((0.06698-0.5)^2+(0.25-1)^2)^{1/2}$
$=(-0.433022+(-0.75^2))^{1/2}$
$=(0.1875063204+0.5625)^{1/2}$
$=(0.7500063204)^{1/2}$
$=0.8660$ Equilateral encoding is not employed by the system in scenarios where there are less than three distinct nominal categories.

Exemplary embodiments of a supervised and unsupervised neural network training algorithm used to create a trained model will be discussed. Those skilled in the art know any variety of machine learning algorithm approaches can be used for the purpose of training system models including, but not limited to support vector machines, genetic programming, Bayesian statistics, decision trees, case based reasoning, information fuzzy networks, clustering, hidden Markov models, particle swarm optimization, simulated annealing, among others.

There are three primary categories of machine learning tasks: classification, regression and clustering tasks.

Classification

Figure 25A:
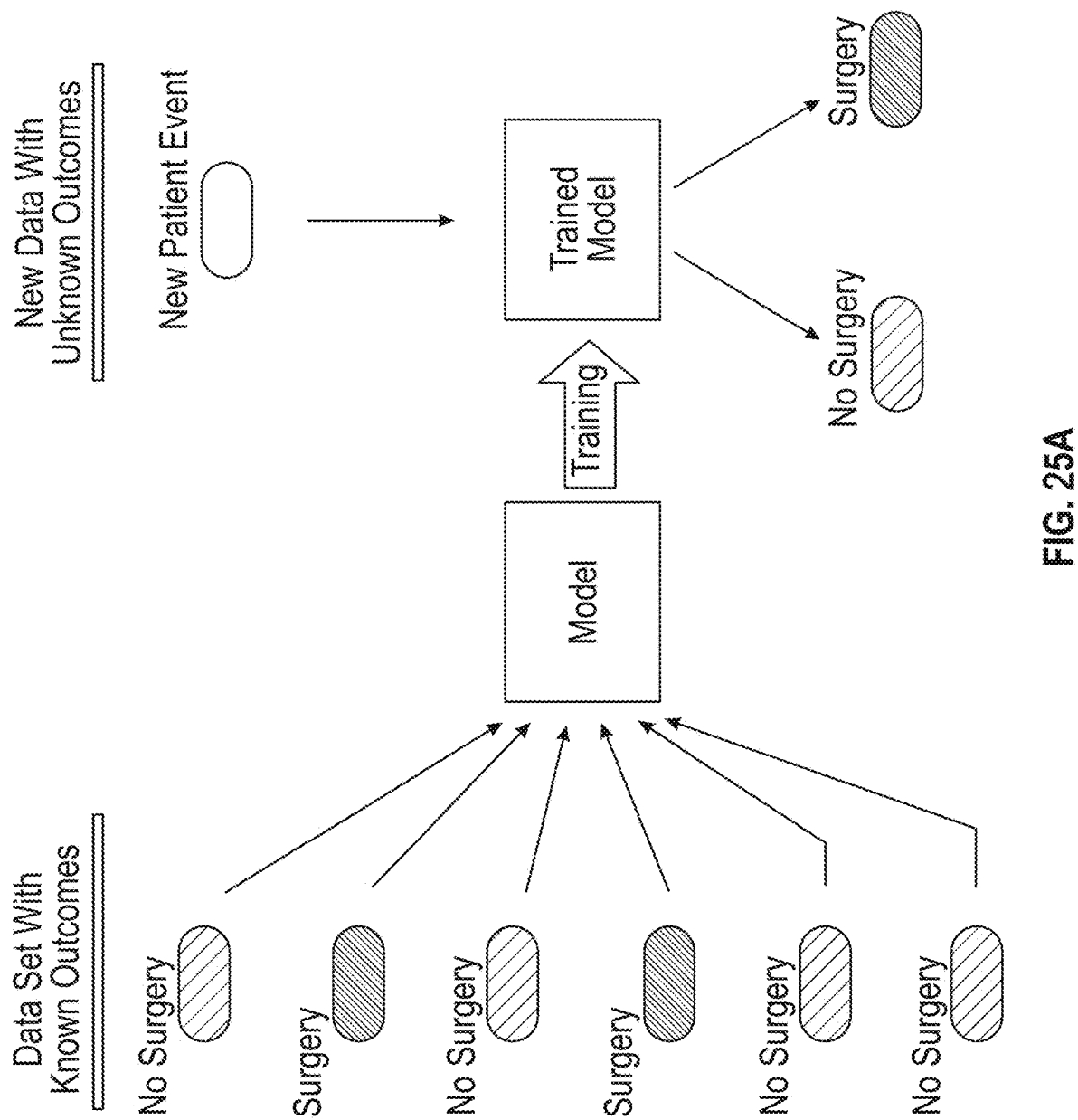
FIGS. 25A-25B are illustrations of a case in which the model is used to categorize the risks of a plurality of patient events.
Figure 25B:
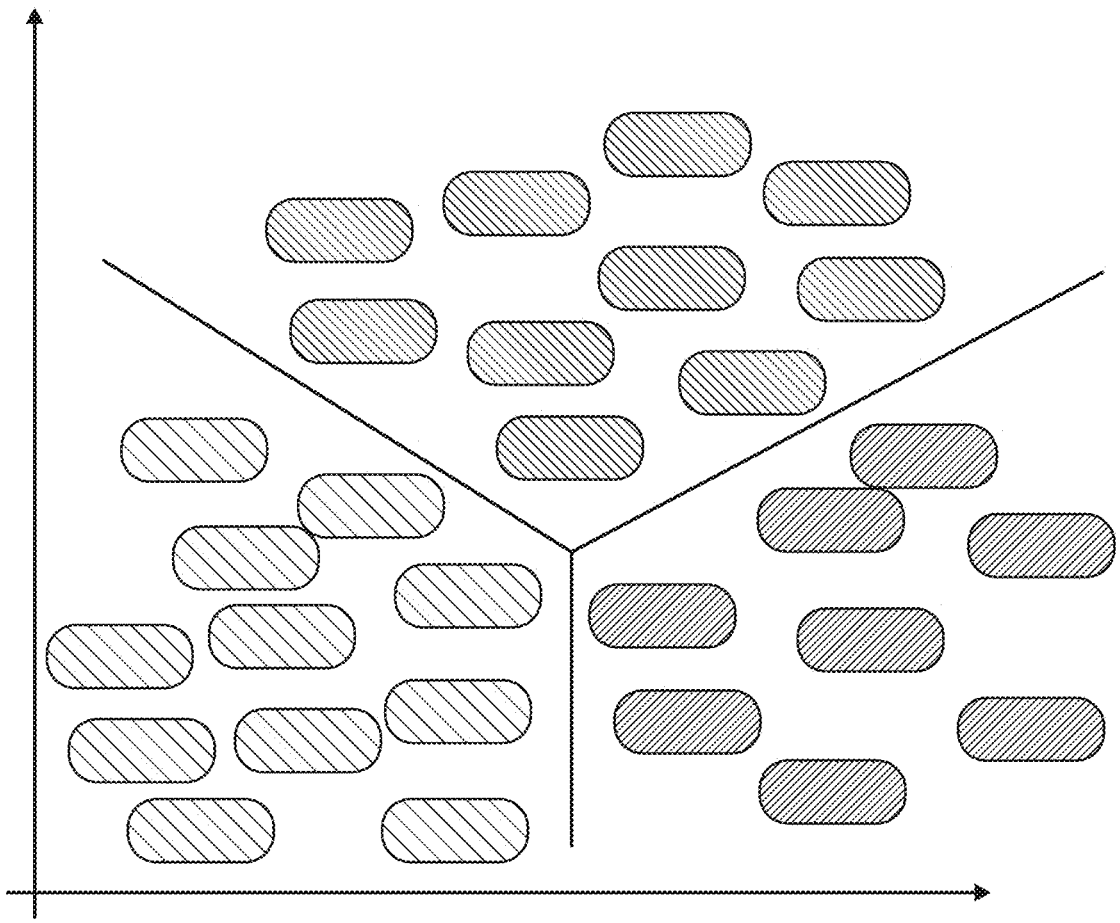

Referring to FIG. 25A-25B, a classification task for predicting surgical intervention of a patient event is shown. The machine learning task entails a two-step supervised learning process which utilizes both input and output data in the model training process. Model construction is done using a representative training data set and the model, once trained is used for making a prediction of new events. The inputs are collected patient data attributes/properties. The output will be predicted categorical risk for surgical intervention.

Regression

Figure 26:
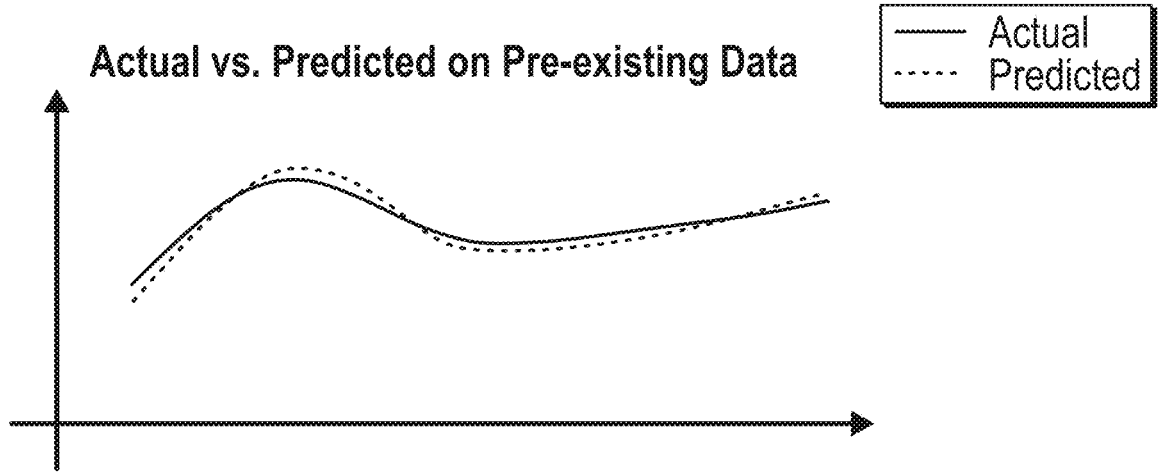
FIG. 26 is an illustration of exemplary regression tasks performed by the TMD.
Figure 26:
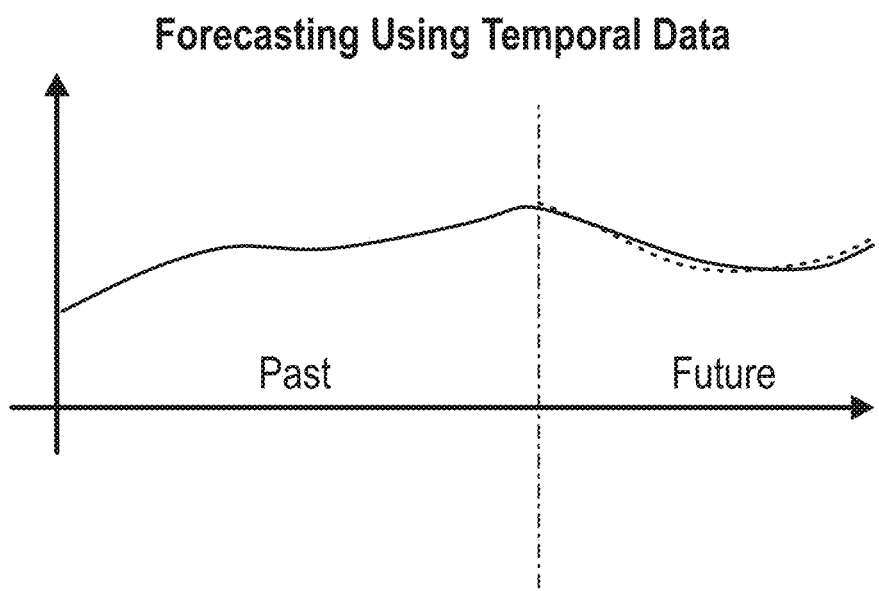

Referring to FIG. 26, a regression task entails a two-step supervised learning process which utilizes both input and output data in the model training process. Model construction is done using a representative training data set and the model once trained, is used to predict the output (numerical or continuous data) for new or unseen cases. The output can be, for example the anticipated length or duration of discharge delay (a quantity of time).

Clustering

Clustering tasks carried out in the server entail an unsupervised learning process. For clustering tasks, categories and outcomes are not known, or if known are not used for model training. Models are trained from the inputs of the data set, again without or ignoring the corresponding outputs, and from these the model training algorithm tries to identify similarities among the input data and cluster the data based on these learnings, so called "unsupervised learning." The backend devices employ each of these categories of machine learning tasks.

Unsupervised Learning

The server 114 in some instances utilizes unsupervised learning techniques (for example Self-Organizing Map (SOM)—also known as Kohenen Map, Singular Value Decomposition (SVD), and Principal Component Analysis (PCA)) for the purpose of dimensionality reduction. This is done to reduce the input data sets from a large number of dimensions to a lower number of dimensions, such as, for example, to two or three dimensions. This is often employed as a pre-processing step in advance of the application of supervised learning methods. By leveraging unsupervised learning for the purpose of dimensionality reduction, the system is able to reduce the processing (training) time and improve model accuracy. Some supervised machine learning techniques work very well on data sets with a low number of dimensions, however, when there are a very large number of dimensions, performance can degrade, the so called "curse of dimensionality." Thus, the employment of dimensionality reduction techniques actually boosts model performance and efficiency for some tasks.

Another exemplary task, for which the server 114 uses unsupervised learning is data visualization. Humans are quite facile with the visualization of data in two or three-dimensional space, however visualizing data with more than three dimensions is not a task for which humans are well suited. One of the ways the system overcomes this is by using its unsupervised learning dimensionality reduction capabilities to make patterns in n-dimensional data more easily perceptible to human end users. Thus, the server's dimensionality reduction techniques significantly boost its ability to make data actionable by making the visibility of meaningful, yet complex patterns, more perceptible to its human end users.

Supervised Learning

The backend devices can use supervised machine learning techniques.

Figure 14:
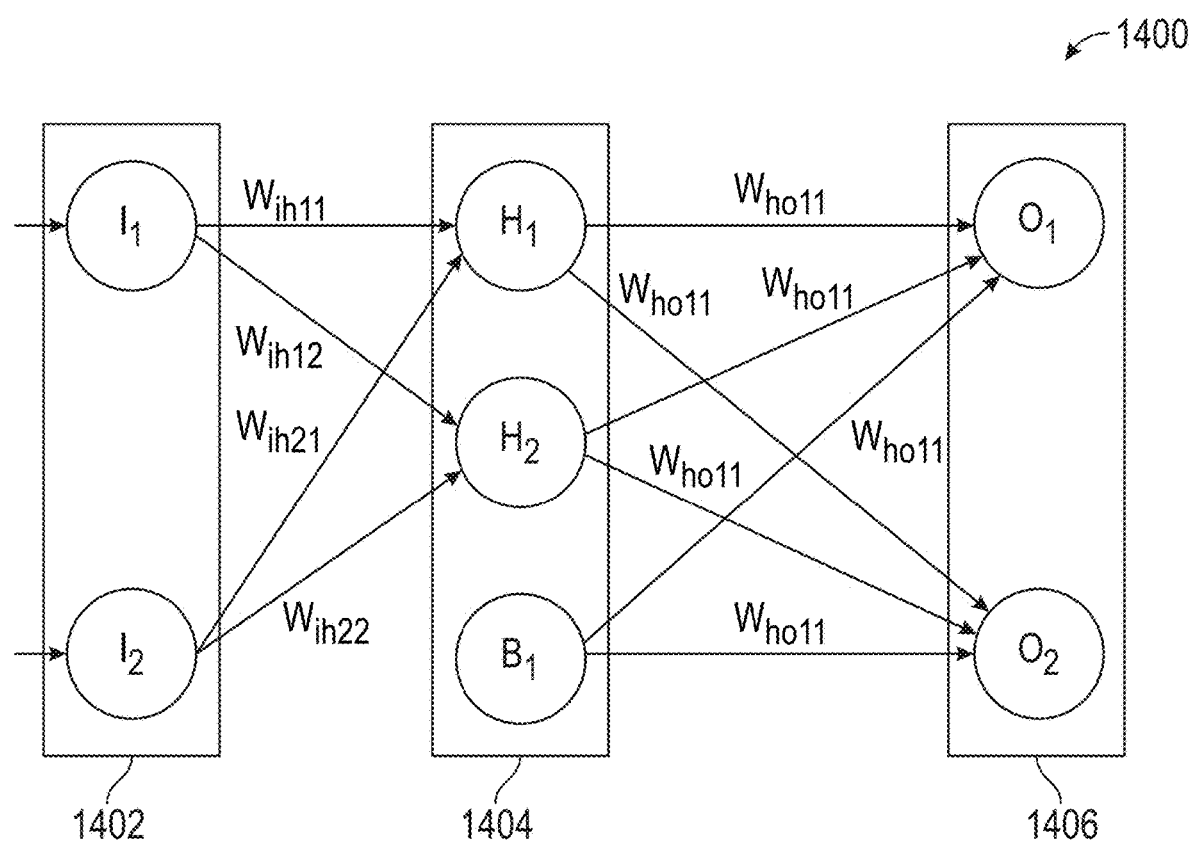
FIG. 14 is an illustration of an exemplary simple feed forward NNM.

Referring to FIG. 14, the backend devices can use a neural network model (NNM) 1400 which includes an input layer 1402, a hidden layer 1404 and an output layer 1406. The input layer 1402 includes input neurons ($I_1$ and $I_2$) which provide input signals to the network without any processing units (processing units, described further herein are comprised of summation and activation functions). The hidden layer 1404 includes hidden neurons ($H_1$ and $H_2$) which provide a means to converge the network's solution leveraging additional processing units (summation and activation functions). At times, if these neurons are not present, the neural network may not be able to output the desired result. The hidden layer 1404 can also include bias neurons (Bi) to provide bias values if there is a requirement for non-zero results. Essentially, they provide a way to obtain a non-zero result even if the input is zero. These most typically do not have any incoming connections, but rather instead, their input values are fixed, for example being fixed with a value of one (1). The output layer 1406 includes output neurons ($O_1$ and $O_2$) containing processing units (summation and activation functions) which provide the means for obtaining the final output of the neural network. A typical neural network employed by the system is comprised of one input layer, one output layer and a plurality of hidden layers (zero or more). The number of neurons the system employs in its neural network input and output layers varies.

In the neural network, connections between neurons have a connection weight or synaptic weight, for example the connection between $I_1$ and $H_2$ has a synaptic weight of $w_{ih\ 12}$. The $w_{ih\ 12}$ notation means the synaptic weight of the connection from input neuron $I_1$ and hidden neuron $H_2$. This synaptic weight denotes the strength of the connection, the higher the weight the higher the strength and vice versa. This synaptic weight determines the effect the synapse has on processing. The synaptic weight is also directional. Said another way, this means the connection from $I_1$ to $H_2$ is different from that from $H_2$ to $I_1$. Thus the notation $w_{ih\ 12}$ not only denotes the neurons that are connected or involved but also the direction of the connection.

Figure 15:
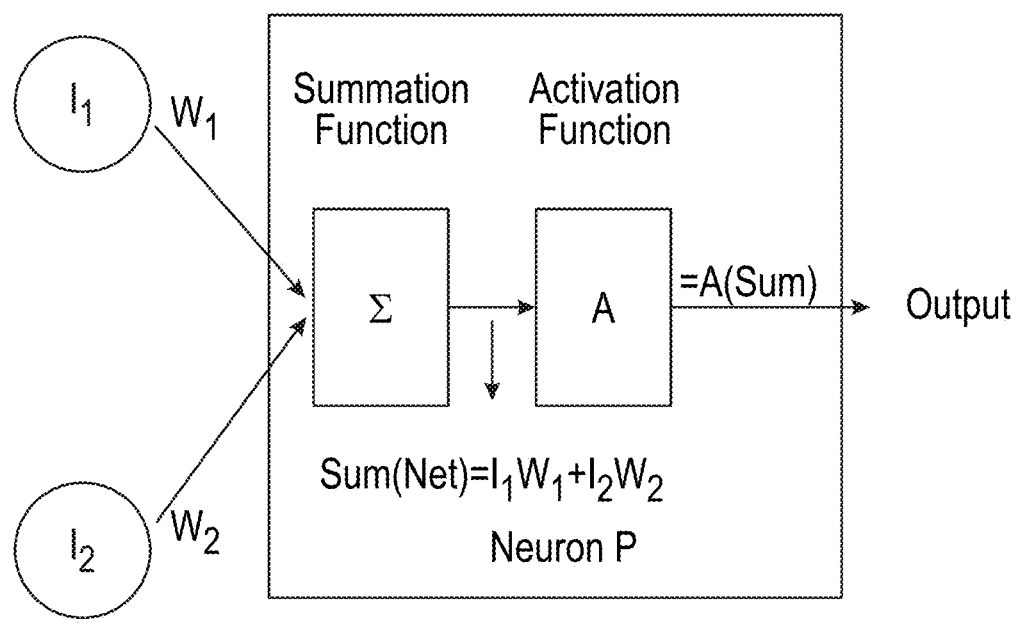
FIG. 15 is an illustration of an exemplary neuron of the NNM.

As shown in FIG. 15, a neural network neuron includes the summation function and activation function. The summation function sums input signals based on their signal strength, or weights. The sum value is also known as Net. The output of the summation function is the weighted sum of input signals. The activation function of a neuron takes the weighted sum of the input signals and performs some calculations to arrive at the output value. Some examples of activation functions used by the system include:

The Sigmoid Function $$f(x) = \frac{1}{1 + e^{-x}}$$

Figure 16A:
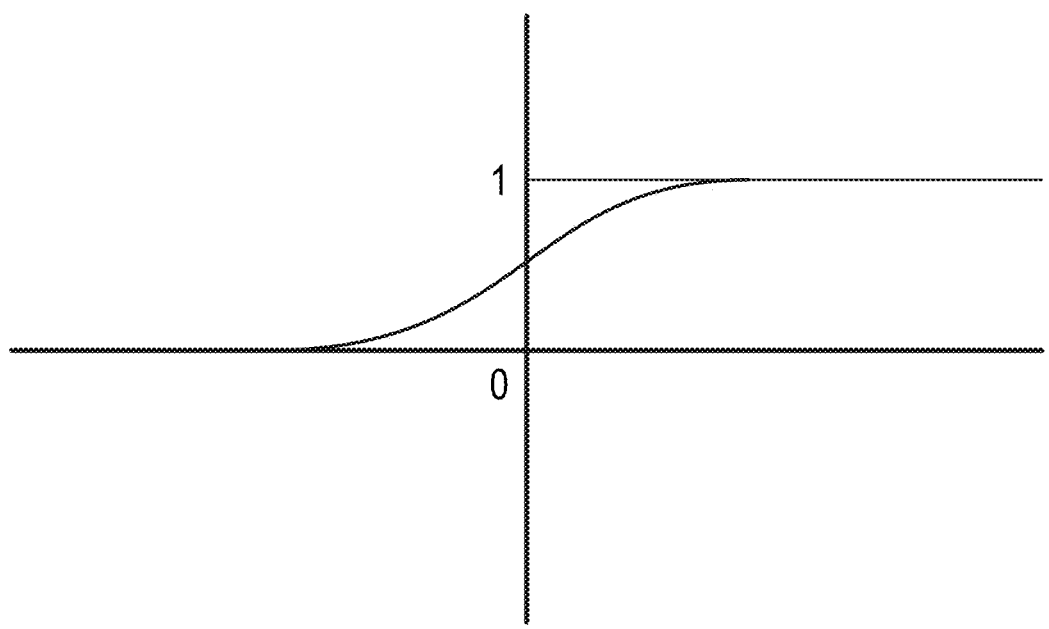
FIGS. 16A-16C are illustrations of exemplary activation functions for the neurons of the NNM.

As shown in FIG. 16A, a characteristic of the sigmoid function is that for all values on the x axis, the function output value (y axis) will lie between 0 and 1. The sigmoid function is used in instances where only positive outputs are expected.

The Hyperbolic Tangent Function $$f(x) = \frac{e^{2x} - 1}{e^{2x} + 1}$$

Figure 16B:
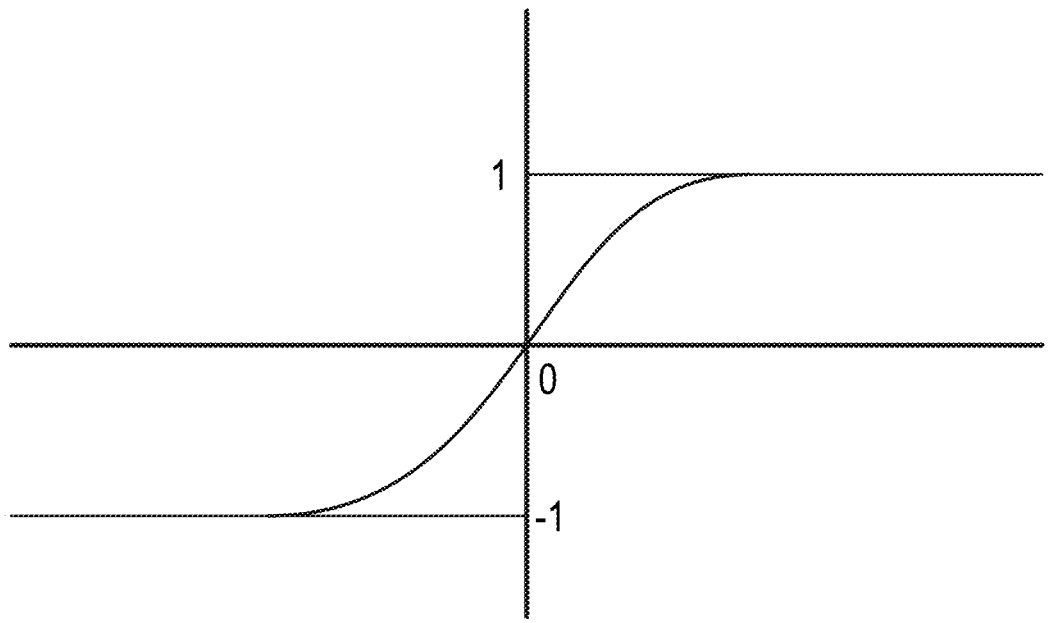

As shown in FIG. 16B, a characteristic of the hyperbolic tangent function is that for all values on the x axis, the function output (y axis) will lie between −1 and 1. The hyperbolic tangent function is used by the system in instances when both positive and negative outputs are expected.

The Linear Function $$f(x) = x$$

Figure 16C:
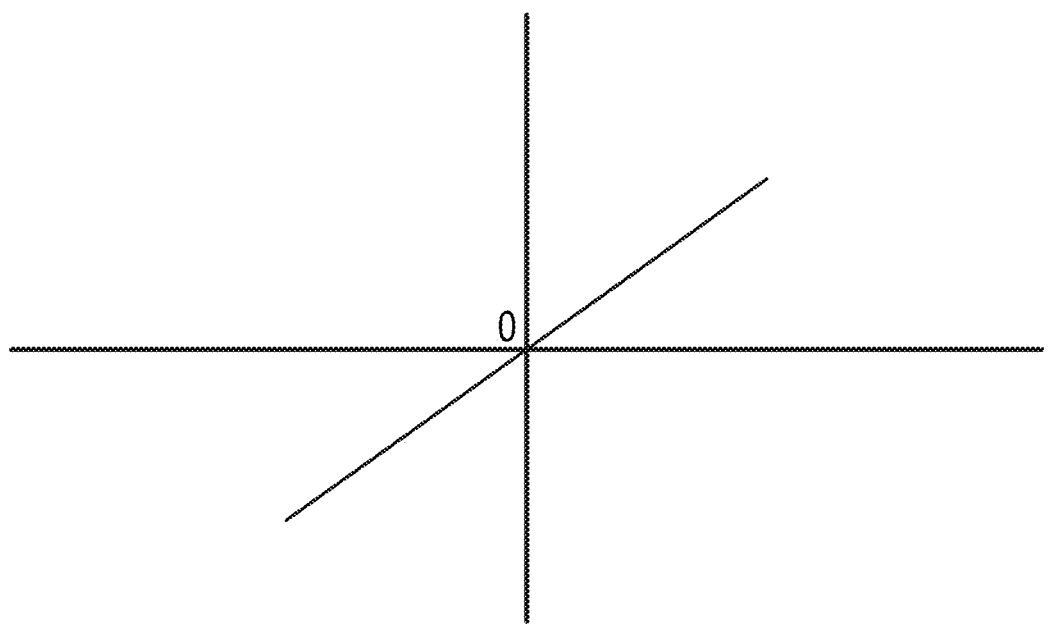

As shown in FIG. 16C, a characteristic of the linear function is that the input and output are the same. The linear function is used by the system in instances where the objective is to replicate the input signal to the output.

The activation functions detailed above are exemplary of activation functions used by the inventive system. One skilled in the art will understand that there are also other activation functions that can be used in neural networks. This disclosure is not intended to be exhaustive, but is intended to describe the fact that the model employs a plurality of activation functions to accomplish its objectives.

Figure 17:
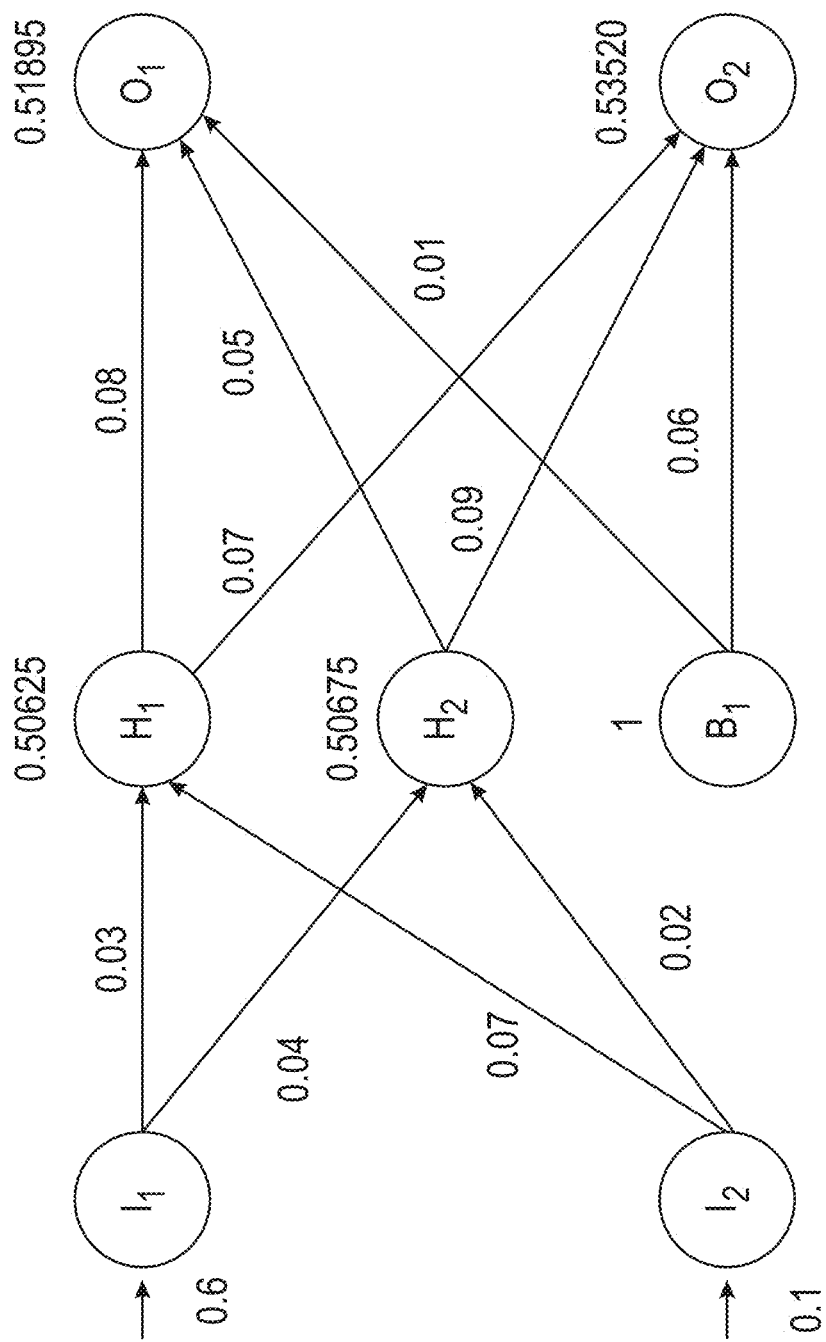
FIG. 17 is an illustration of exemplary computations of the NNM.

A NNM is a neural network architecture with a particular structure tailored to a particular problem statement. An exemplary problem statement the server's 114 neural networks model is the prediction of whether a given patient event is likely to require surgical intervention or not (in this example, a categorical output is predicted). Using a trained NNM, the server 114 predicts the likely outcome using a plurality of the properties or attributes of the pending patient event (the inputs). Each model in the system contains input, output, bias and hidden neurons. The input and output neurons are required whereas the bias and hidden neurons are optional depending on the nature of the specific problem statement and its requirements. Each model also has a structure. The exemplary neural network herein depicted in FIG. 17 is demonstrative of a feed forward structure, however other possible neural network structures or architectures include, but are not limited to, Convolutional Neural Network (CNN), ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), Radial Basis Function Network, Recurrent Self Organizing Map (RSOM), Self Organizing Map (Kohonen), among others. Feedback networks, for example Elman and Jordan Networks, are at times leveraged by the system particularly in instances where the sequence of events (order of data) is material. Each neural network model also has a defined activation function. In the exemplary neural network of FIG. 17, the activation function is the sigmoid function. Prior to model training, the model's neurons and their structure as well as the activation function are defined. The training of a model starts with the random selection of a set of initial synaptic weights. During the training process, the synaptic weights are updated after each training iteration (see further description provided herein). The below describes how the values at the neural network nodes $H_1$, $H_2$, $O_1$ and $O_2$ are calculated for given inputs $I_1$ and $I_2$ and a given set of synaptic weights (synaptic weight values for this example are those shown in FIG. 17). This calculation process is used during each model training iteration and subsequently when the trained model is used to make predictions from previously unseen input data:

$H_1$

Sum = 0.6 ∗ 0.03 + 0.1 ∗ 0.07

= 0.018 + 0.007

= 0.025

Output = $A$(Sum) = 0.50625

$H_2$

Sum = 0.6 ∗ 0.04 + 0.1 ∗ 0.02

= 0.024 + 0.002

= 0.027

Output = $A$(Sum) = 0.50675

$O_1$

Sum = 0.50625 ∗ 0.08 + 0.50675 ∗ 0.05 + 1 ∗ 0.01

= 0.0405 + 0.0253375 + 0.01

= 0.0758375

Output = $A$(Sum) = 0.51895

$O_2$

Sum = 0.50625 ∗ 0.07 + 0.50675 ∗ 0.09 + 1 ∗ 0.06

$$= 0.0354375 + 0.0456075 + 0.06$$
$$= 0.141045$$
$$\text{Output} = A(\text{Sum}) = 0.53520$$

During the training process, the synaptic weights are adjusted to minimize the error of the output. Thus, the final synaptic weights of the trained model are only known once model training is complete. After successful training of the model, the finalized synaptic weights are then used to make predictions.

Training the NNM

The server 114 applies machine learning algorithms to modify the synaptic weights of each model's connections as it learns the patterns in the data. Thus, trained models in the system are system models with finalized synaptic weights that result in the most minimal error. Training algorithms along with representative data sets presented to each of the models for the purpose of training are employed by the system to update the synaptic weights of each model's connections with values that minimize the error.

There are two types of error that pertain to neural networks. The first is Local Error (E). Local error is the actual output value computed by the neural network subtracted from the ideal value (i.e. the output value in the training data set). This error is "localized" to particular output neurons, hence the name local error. The other type of error is the error of the neural network, also called network error or global error. The global error is the cumulative effect of the error at each of the outputs (the local error for each output). There are a few types of global error which are briefly discussed below.

Mean Square Error (MSE)

$$\frac{\Sigma_n E^2}{n}$$

The mean square error (MSE) is the sum the square of all local errors divided by the total number of cases.

Sum of Square Errors (ESS)

$$\frac{\Sigma_n E^2}{2}$$

The sum of square errors (ESS) is the sum of the square of all local errors divided by two (2).

Root Mean Square Error (RMS)

$$\sqrt{\frac{\Sigma_n E^2}{n}}$$

The root mean square error (RMS) is the square root of the MSE.

The system generally uses MSE, however, in some specific instances the other methods for determining the global error are used.

To more formally state the objective of using machine learning to train the models in the system, it is most accurate to say that the system employs machine learning algorithms and training data to adjust the synaptic weights for the connections in each model such that the global error is less than a pre-established level. The system is configured with acceptable global error levels that balance the tradeoffs of model overtraining (acceptable global error level too low) and model undertraining (acceptable global error level too high).

Figure 18:
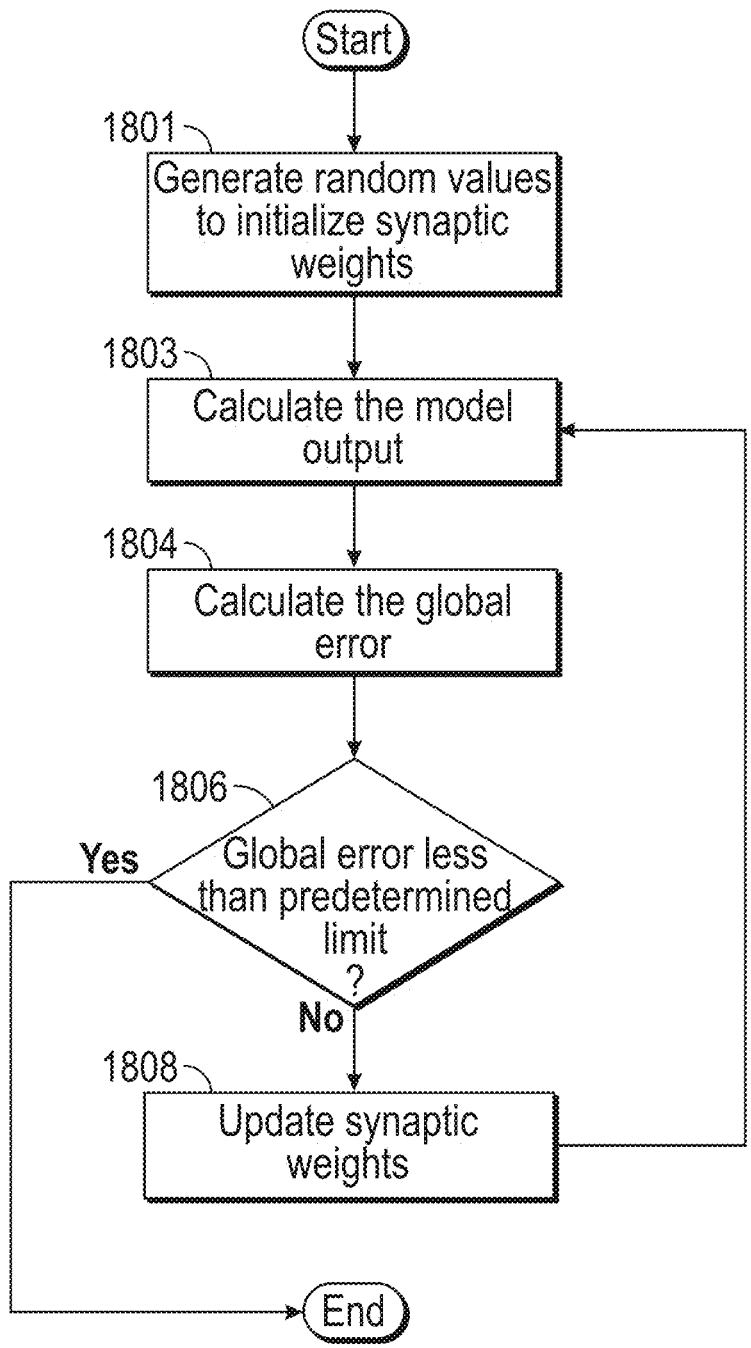
FIG. 18 is a flow diagram illustrating exemplary operations of the system for training the NNM.

Referring to FIG. 18, the approach for training the NNM based upon training data will be discussed. The training data is quantifiable outcomes (surgical intervention required or not) of a plurality of past patient events and patient attributes of each of the past patient events. Initially, at 1801, values of the plurality of synaptic weights are assigned to random values. At 1803, the output values of the model are calculated for the current "row" or case in the training data being used for the current training iteration (i.e. "row" being the one transaction or case used for the current training iteration out of the available transactions in the training data set) using the initial random synaptic weights. At 1804, the global error for this iteration of the NNM training process is calculated. Particularly, a local error at each of the output(s) is calculated, which is the difference between each output value of the NNM on this iteration and the corresponding actual (known) quantifiable outcomes from the current "row" in the training data set. The global error is then calculated by summing all of the local errors in accordance with MSE, ESS and/or RMS discussed above. If it is determined that the global error is not less than a predetermined acceptable global error (NO at 1806), the values of the synaptic weights are adjusted at 1808, and a new training iteration using another patient event from the training data set begins (at 1803). As part of this next iteration, the global error is again calculated at 1804. Here, if the global error is never reached after a number of iterations, the model can be revised, such as changing the number of hidden layers, neurons, etc., and the training process can be attempted again. When it is determined that the global error is less than the predetermined acceptable global error (YES at 1806), the trained model is then subjected to validation discussed later.

Different machine learning algorithms as well as different global error calculation methods can be employed to update the synaptic weights. Some of the machine learning algorithms the server can be configured to employ include ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), among others. Machine learning algorithm selection is determined based on a number of factors some of which include accuracy of the algorithm, the computation resources available and those required of the algorithm, the available or ideal training time duration, among others.

Figure 19:
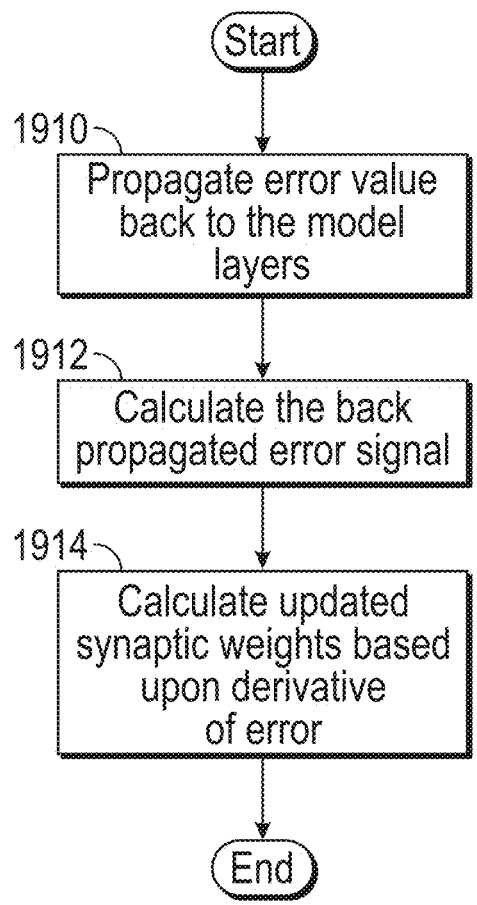
FIG. 19 is a flow diagram illustrating exemplary operations of the system for propagation training (updating the synaptic weights between iterations) of the NNM.

Training the system models is an iterative process referred to as propagation. As discussed above, the process begins by using randomly assigned synaptic connection weights to compute the outcome of the model (1803). Using the known output values for cases in the training data set and the output values computed by the model, the local error at each output, and subsequently the global error of the network is determined (1804). If the global error is not below the pre-established acceptable global error rate a new iteration with updated synaptic weights will ensue. The process for updating the synaptic weights (1808) is referred to as propagation training. As already discussed, the system can be configured to employ one of a variety of methods (algorithms) for updating the synaptic weights during the training process for a given model. Referring to FIG. 19, a gradient-decent procedure can be used to update the synaptic weights on each training iteration. At 1910, the error value is propagated to the model layers. The gradient-decent procedure is used to determine the direction of change of the synaptic weight(s) that will minimize error on the next iteration. Doing this requires model neurons to use differentiable activation functions, such as those already previously discussed herein. At 1912, the back propagated error signal is determined by calculating the error gradient (gradient-decent procedure). The error gradient is the value of the instantaneous slope at the current point on the error function surface plot. Said another way, the error gradient is the derivative value of the error function surface plot, the plot of the error values that correspond to different synaptic weights. The proportion of the error gradient that is used in each iteration of the propagation process is called the learning rate and can be configured in the system (essentially, how much of the derivative value should be applied to update the synaptic weights on each model training iteration). This procedure can vary depending on the propagation algorithm employed by a given model in the system. The larger the learning rate, the larger the synaptic weight changes will be on each iteration and the faster the model will learn. However, if the learning rate is too large, then the changes in the synaptic weights will no longer approximate a gradient decent procedure (a true gradient decent is predicated on infinitesimal steps) and oscillation of the synaptic weights can result (no learning at all). Conversely if the learning rate is too slow, training of the model will be a very lengthy process utilizing large amounts of compute time. The learning rate that is used for training the system models is one that results in brisk learning without triggering oscillation. When the system is configured with optimal learning rates the fastest training of each model is achieved with the smallest compute training time expenditure.

The model propagation training process utilized by the system can also employ the concept of momentum to deal with the challenge of local minima that can complicate backpropagation (the process of following the contour of the error surface with synaptic weight updates moving in the direction of steepest decent), for example, when the network architecture includes a hidden layer. Momentum is the concept that previous changes in the weights should influence the current direction of movement in the weight space (essentially the percentage of previous iteration weight change to be applied to the current iteration). As such, the inclusion of the momentum parameter can help networks employed by the inventive system to "roll past" local minima. In addition, the inclusion of the momentum parameter can also help speed learning, particularly when long flat error surfaces are encountered. At 1914, the updated synaptic weights are calculated based upon the derivative of the error, the defined learning rate and the momentum parameter.

Training and Validation of System Models

Figure 20:
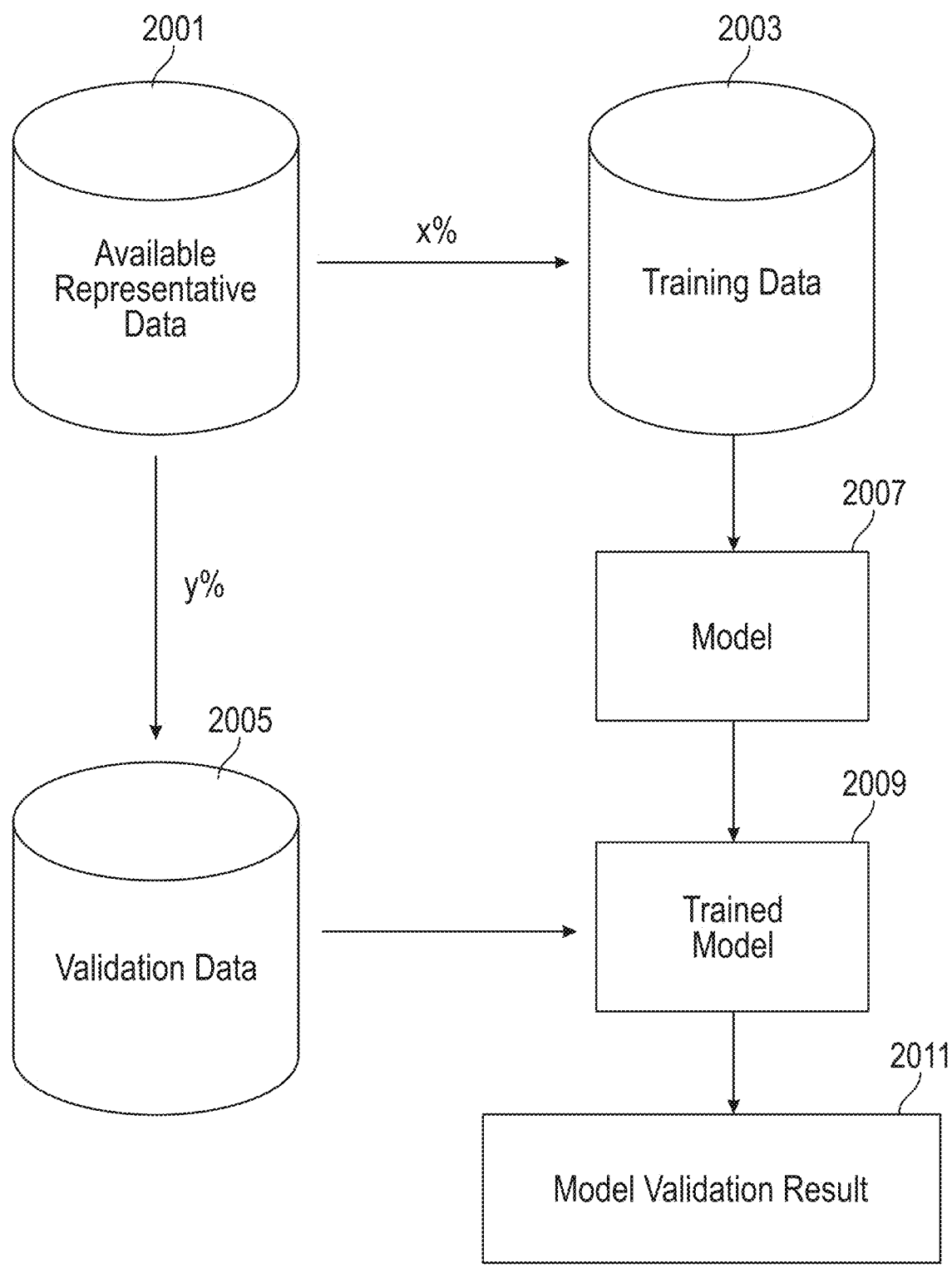
FIG. 20 is block diagram illustrating high level operations of the process for training the NNM and validating the trained NNM.

The training process for the NNM employs a representative data set, which can be a plurality of past patient events as discussed above. Referring to FIG. 20, the cases in the representative data set 2002 are divided into two unique data sets by some ratio or percent x allocated to the training data set 2004 and percent y allocated to the validation data set 2006. The ratio of cases allocated to the training data set 2004 versus those allocated to the validation data set 2006 varies. Before the allocation of cases to the training data set 2004 or the validation data set 2006, an optional step of data shuffling can be carried out by the system to help ensure all types of data in the representative data set 2002 gets distributed to both the training 2004 and the validation 2006 data sets. The training data set 2004 was used to train the NNM 2008 as discussed above. The validation data set 2006 can be used to validate the trained NNM 2010 because the real outcome of each case in the validation data set is known. The server can generate an output value (model validation result) 2012 of the trained NNM 2010 for each past patient event of the validation data set 2006, wherein each of the output values 2012 represents a calculated quantifiable outcome of the respective patient event. Then the server can determine if the output values 2012 correspond to the quantifiable outcome within the predetermined global error.

The training data set 2004 along with the defined system models, the selected machine learning training algorithms and the method each uses for global error calculations, in conjunction with the pre-defined acceptable global error rates are used to train the NNM starting with randomly assigned synaptic weights for each model's neuronal connections. The requisite number of synaptic weight calculation iterations are executed until an acceptable global error level is obtained. Subsequently, the trained model 2010 is then used to predict the outcome for cases in the validation data set 2006, the so called "unseen data" (from the perspective of the trained model). Because the real outcome of each case in the validation data set is known, at this point a validation report can be generated comparing the predicted results with the actual results and the findings can be used to determine the validity of the trained model, essentially whether it is successfully predicting the actual outcomes for the cases in the validation data set. The end result is an assessment of how well the trained system model performs on unseen data.

Using the Trained NNM

Returning to FIG. 11A, the backend device receives a plurality of input attributes of a new patient event. This data may come from a client device, from the database at the server, or a combination. The data is pre-processed (for example, normalized) to generate an input data set, and the data is input into the trained model 1107 which then generates an output value. The output value is then post-processed (for example, de-normalized). Finally, the output value is classified into a surgical intervention risk category (classification task) or a value such as the probability of surgical intervention (regression task) to predict the outcome. For example, in the simplest case the de-normalized output value can be a Boolean value (surgical intervention or no surgical intervention). In another case, the output value can be a probability of surgical intervention occurring. In this case, the TMD or server may assign probability ranges which define particular categories.

Unsupervised Learning

Figure 21A:
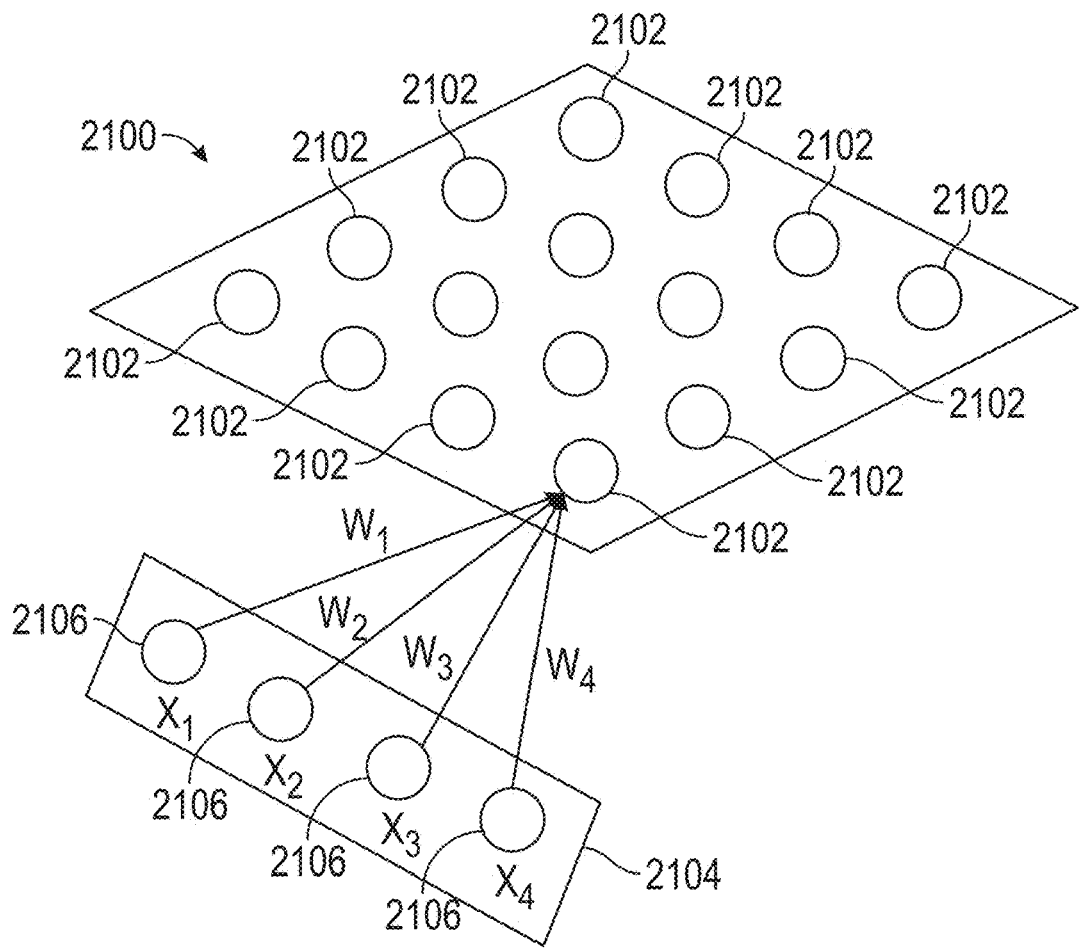
FIGS. 21A-21B is an illustration of an exemplary Self-Organizing Map (SOM) and the input data set to the SOM network.
Figure 21B:
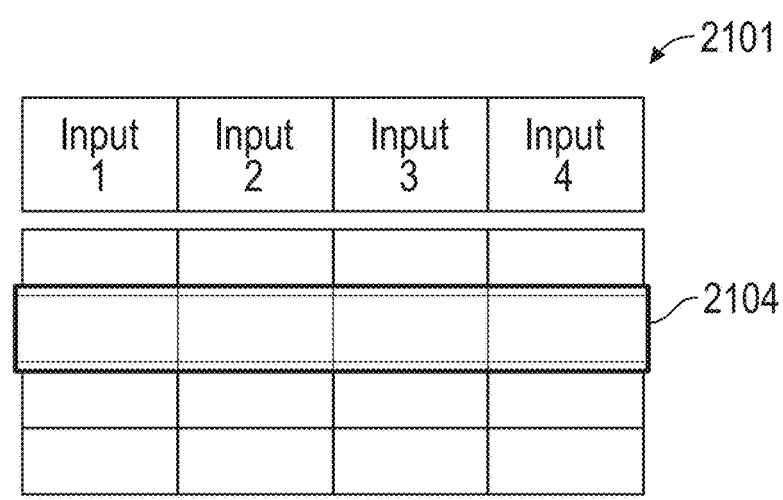

The server can also use unsupervised learning techniques as well as supervised learning techniques to determine the group or cluster to which particular patient events belong. Referring to FIGS. 21A-21B, a Self-Organizing Map (SOM) 2100 is an unsupervised neural network that consists of a grid or lattice of nodes 2102 with a certain structure which may be one, two or three dimensional. The SOM 2100 includes a grid of nodes 2102 on some two (or three) dimensional plane where each node has an x and y coordinate (and z coordinate in the case of a three-dimensional node network), a so called fixed topological position, and an input layer 2104 with various input nodes 2106 that are used to provide input to the SOM network 2100. The input layer 2104 can be a random row from the training data set 2101

Figure 21C:
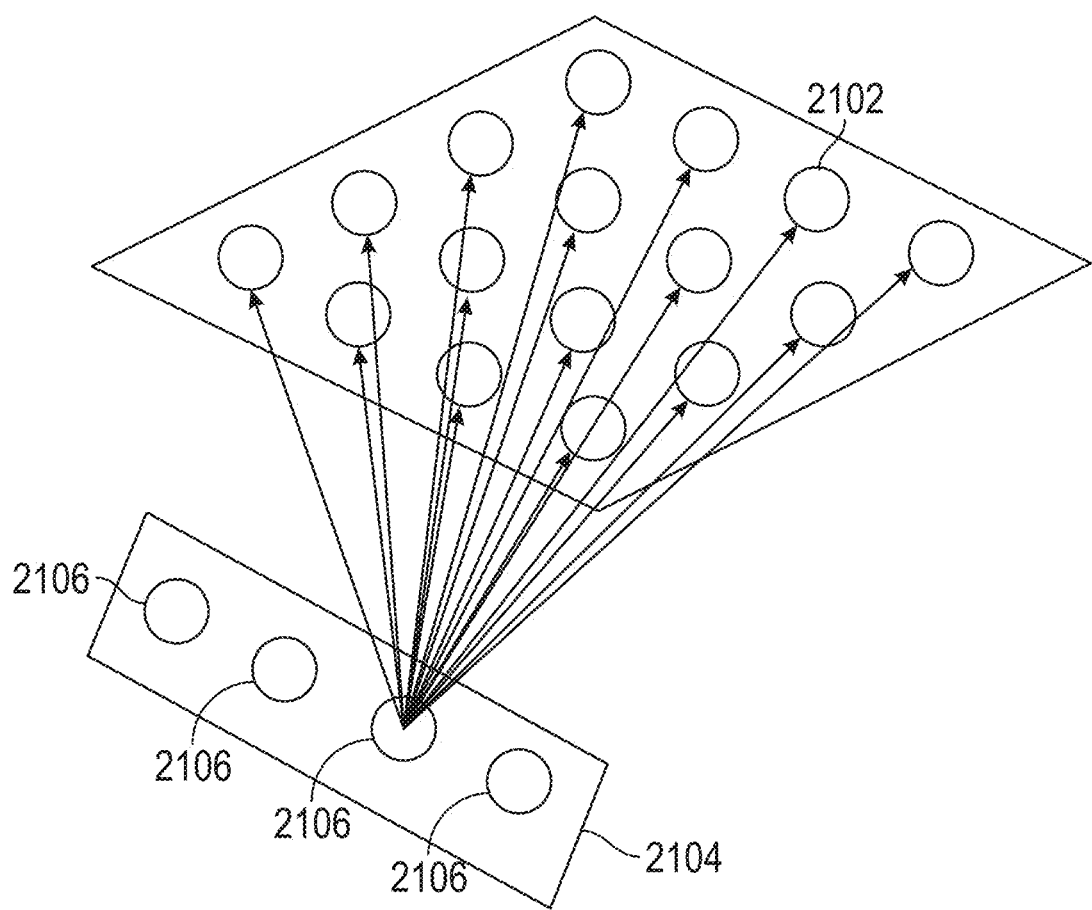
FIG. 21C is an illustration of how each node of the SOM network will contain the connection weights of the connections to all connected input nodes.

(FIG. 21B). The specific number of inputs is dependent on the specifics of the data set. Each input node is connected to every node of the two (or three) dimensional SOM network (FIG. 21C) and each connection has a synaptic connection weight (w), much like that in supervised networks. Each node 2102 of the SOM network 2100 will contain the connection weights of the connections to all connected input nodes. As partially shown in FIG. 21C, each SOM network node 2102 is connected to all input nodes 2106, thus each node of the SOM network will have an equivalent number of connection weights (equivalent to the number of input nodes).

Figure 22:
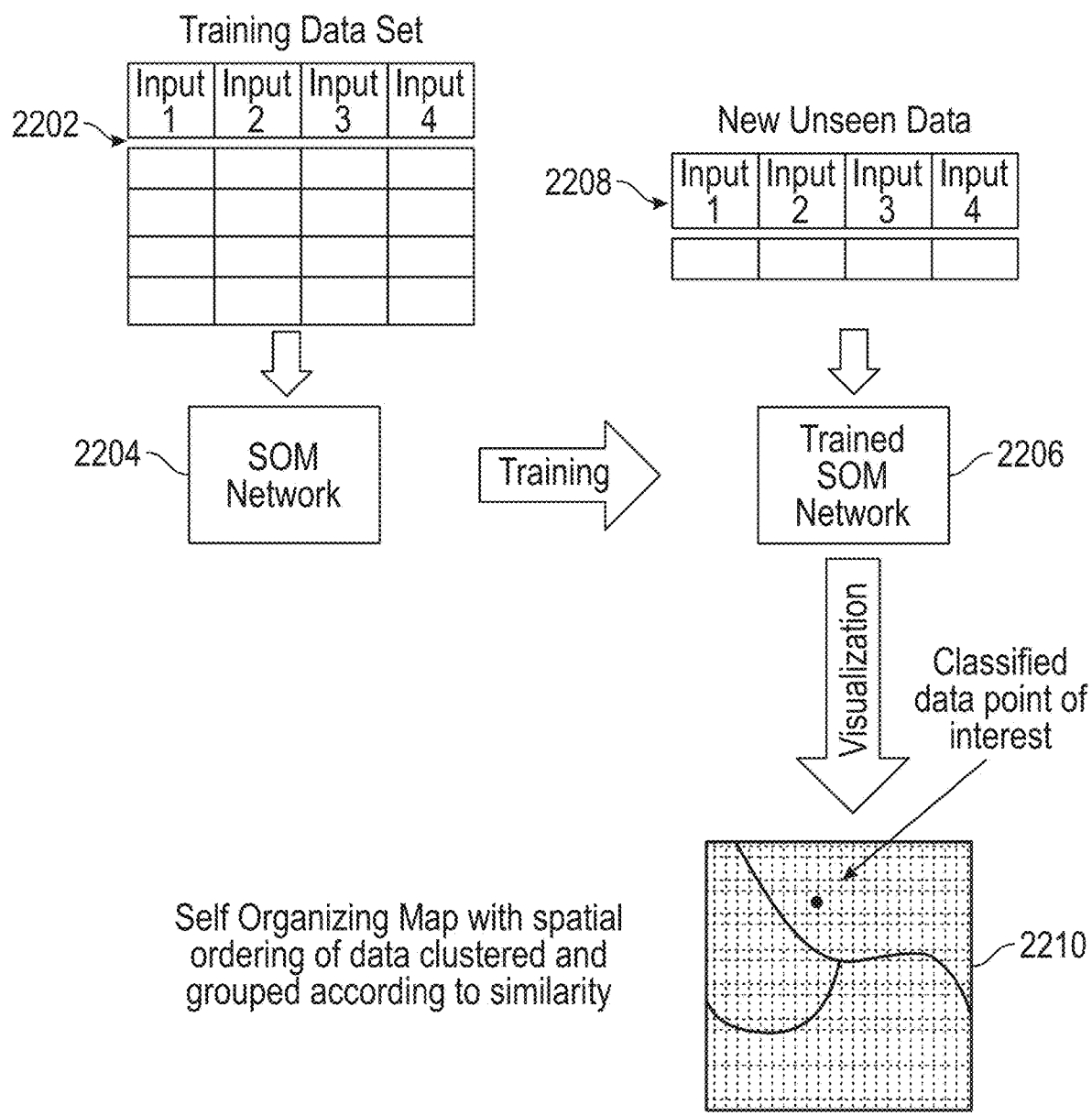
FIG. 22 is a block diagram illustrating high level operations of the process for training the SOM.

A representation of the process for creating, training and using the trained SOM model is shown in FIG. 22. A training data set includes a plurality of patient attributes of past patient events. The training data set 2202 is input into the SOM network 2204. The SOM network 2204 is trained to generate the trained SOM network 2206. New data 2208 is input into the trained SOM network 2206. The output of the trained SOM network can be an SOM image 2210 that shows spatial ordering of data clustered and grouped according to similarity such that that the group or cluster to which a given data point of interest belongs can be determined. The SOM image 2210 can be rendered on a client device.

Figure 23:
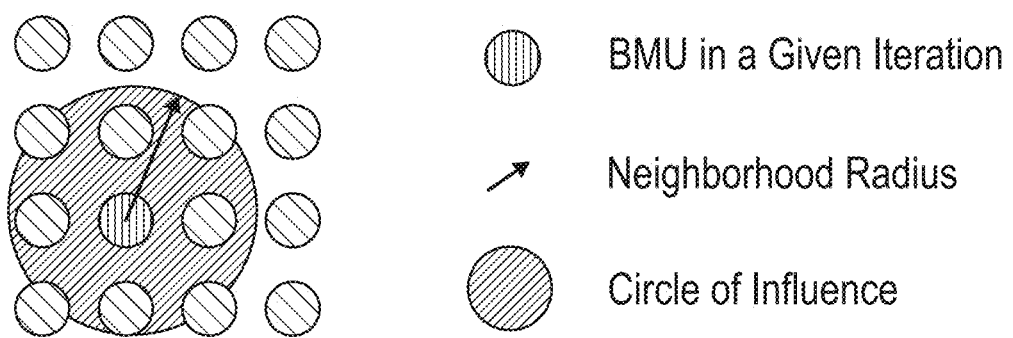
FIG. 23 is an illustration of the process for training the SOM network.

Referring to FIG. 23, the first step in SOM model training is to initialize values of the plurality of synaptic connection weights to random values. The next step is to randomly select one row (one past patient event) from the training data set, which is most typically normalized (for this purpose) and determine which of the plurality of network nodes is the best matching unit (BMU) according to a discriminant function such as a Euclidean Distance. When a node is selected and compared with the row selected from the training data, the Euclidean Distance which serves as our discriminant function for this competitive network, is calculated, though others, for example, Manhattan distance, can be used. This process is repeated for each SOM node. The SOM node with the smallest Euclidean distance (or said another way, the neuron whose weight vector comes closes to the input vector) will be designated as the BMU for that randomly picked input data row. Thus, the BMU is the closest SOM network node to the randomly picked input data row. Next, the neighborhood radius, or the so called neighborhood kernel (function), is calculated. Usually the Gaussian function is used, although the Bubble function is another possibility. The neighborhood radius allows for the determination of the specific BMU neighborhood nodes in the SOM network to which connection weight updates should be applied on the next training iteration. All nodes within the "circle of influence" corresponding to the neighborhood radius are updated. The procedure used to calculate this radius value is shown below:

$$r(n) = r_0 e^{-\left(\frac{n}{\lambda}\right)}$$

$r_0$=initial radius
n=iteration number
$\lambda$=time constant

Usually a large initial radius value is selected for the purpose of having the almost the entire network covered. n is the iteration number and lambda is a time constant (iteration limit). This calculation of the radius is basically a decreasing function whereby the value of r will diminish over the course of the training iterations, another way of saying the topological neighborhood decays with distance or that the topological neighborhood decreases monotonically over the period of iterations. Hence a greater number of SOM nodes are updated early in the training process, and on subsequent rounds there is a smaller number of nodes in the neighborhood of the BMU that get updated. At this point in the training process the connection weights are updated for the BMU and those nodes in the neighborhood of influence. The connection weight update equation is as follows:

$$W_k(n+1) = W_k(n) + \alpha(n) h_{ck}(n)[x(n) - W_k(n)]$$

Where n is the iteration number, k is the index of the node in the SOM network, and $W_k(n+1)$, is the updated connection weight (weight vector of node k) for the next training iteration which is calculated as shown using $\alpha(n)$, a monotonically decreasing learning coefficient (learning rate), $h_{ck}(n)$, the neighborhood kernel (function)—something that, for simplicity can be called the influence factor, and $[x(n)-W_k(n)]$, the difference between $W_k(n)$, the old weights (the weights on the current training iteration), and $x(n)$, a randomly selected row or input pattern from the input data that was used on the current iteration.

Thus, a simplistic way of stating this is the new weights for the next training iteration are calculated by adding the old weights from the current training iteration to the product of the learning rate multiplied by the influence factor multiplied by the difference or delta between the old weights and the randomly picked input data used for a given training iteration. Note the influence factor is often a radial based function such as the Gaussian function (though as mentioned earlier, other types of radial functions can also be used) and this is the reason why the nodes closest to the BMU have or receive more influence than those further away from the BMU which are updated by a smaller amount. Also, in regards to the learning rate, it decreases (decays) over time, meaning that in the earlier phases of the training process, there is more learning, but over the training period the learning effect will decrease in each sequential iteration. The delta between the old weights and the randomly picked input data used in a given training iteration is a determinant of how different the current SOM network node is in comparison with the randomly picked input data row used on the given training iteration. Hence, these three factors are the determinants of the updated connection weights that should be used on each subsequent training iteration for the SOM network nodes. So the learning rate and the influence factor decay over the period of iteration to allow for the proper convergence of the solution such that a stable result can be obtained at the end of training. The training process is repeated for a fixed number of N iterations to generate the trained SOM network.

Figure 21D:
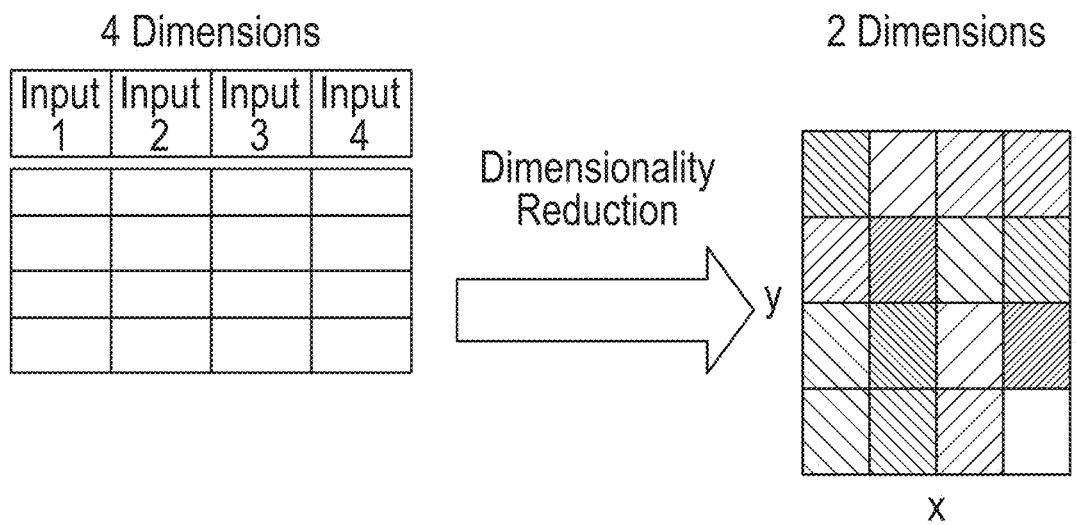
FIG. 21D is an illustration of the SOM network used to reduce dimensionality of the input data sets.

Returning to FIG. 11B, an exemplary data set includes a plurality of data [1, 2 ... N], and a number of properties [1, 2 ... N] for each data. The data set can be a plurality of past patient events and the properties can be a number of attributes of each past patient event. The high dimensionality of the data sets can make visualization of the data difficult. As illustrated in FIG. 21D, the dimensionality reduction aspect of SOM networks allows data of high dimensionality to be projected to a two-dimensional grid which expresses the similarity of samples and the distance between them. However, the mere position on the map cannot sufficiently embody the complexity of an n-dimensional vector. The challenge of information representation is a mature area of research and numerous approaches of displaying multidimensional multivariate data have been proposed as discussed in the article entitled "30 Years of Multidimensional Multivariate Visualization" authored by Wong and Bergeron (1997), the contents of which are hereby incorporated by reference. One such technique therein described utilized by the system is Scalable Vector Graphics (SVG), an XML markup language for describing two-dimensional vector graphics, both static and animated.

Figure 24:
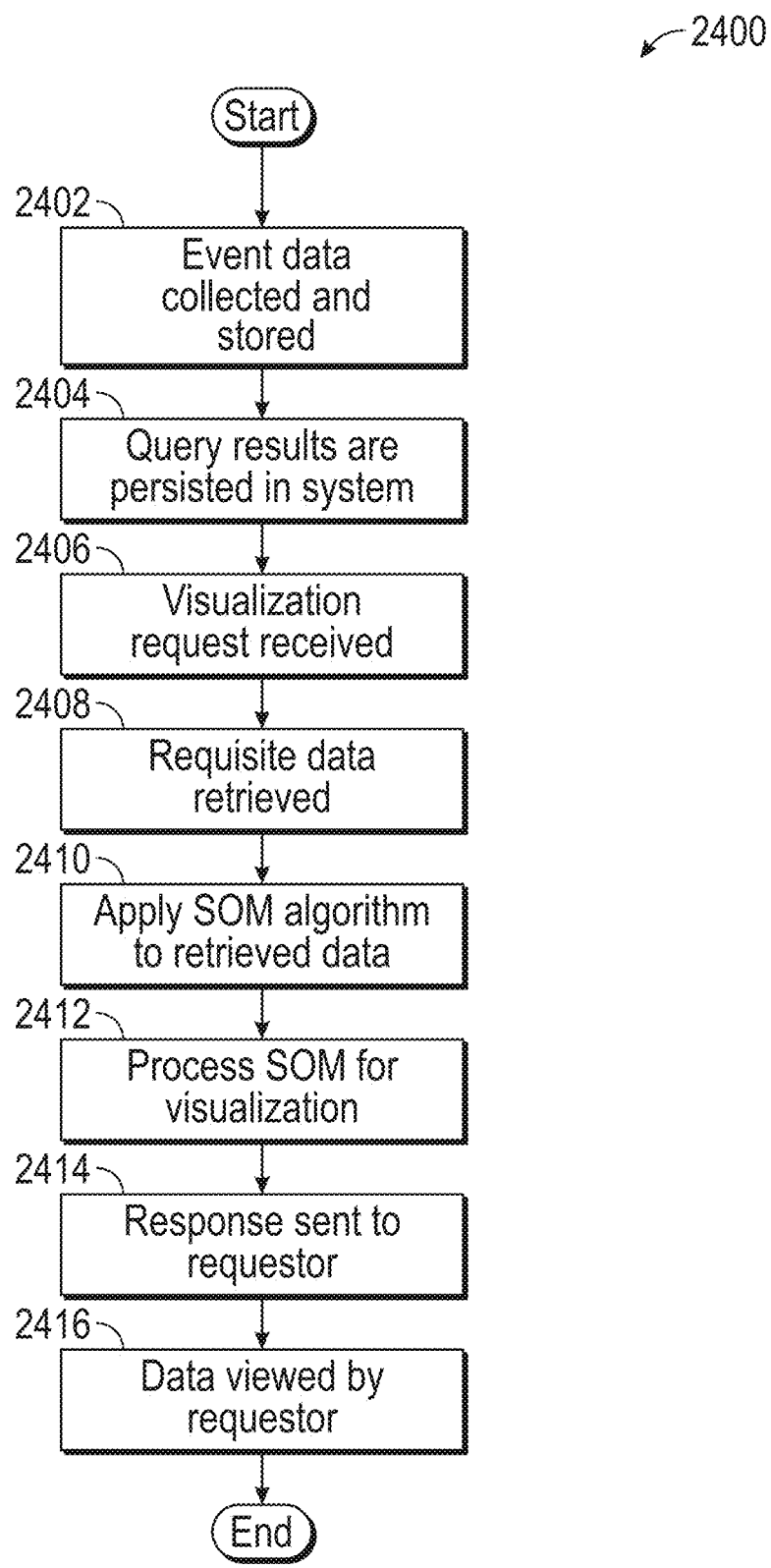
FIG. 24 is a flow diagram illustrating exemplary operations of the system to generate the graphical image including the visualization.

Referring to FIG. 24, an exemplary process 2400 by which the system can employ an SOM network to take a data set of events defined by n-dimensional input attributes and generate a visualization of the results after passing the data into a SOM network will be discussed. At 2402, event attributes are collected and stored. Particularly, the DCE collects imaging data and transmits it to the backend devices. This data can be stored in the database at the server with respect to the patient as discussed above. At 2404, the server (or TMD) can maintain query results in the memory. At 2406, the TMD receives a visualization request from a client device or web browser via the network with query parameters. At 2408, the TMD sends a data request with the query parameters to the server, which retrieves from the database the data sets consistent with the request. At 2410, the server inputs the data sets to the trained SOM network. At 2412, the server generates a visualization or graphical image based upon the output from the SOM network. At 2414, the server sends the graphical image to the TMD, which either sends it to the client device and/or renders the image on a display of a website. The output produced can be groupings or clustering of events with similar characteristics, much like the classical "market segmentation" or "document classification" tasks for which SOMs are widely employed. This SOM output can be generated from a variety of vantage points or perspectives with one or more specified criteria, for example, specific time ranges, or for only events requiring surgical intervention, or only for a particular subset of events processed by a particular employee, a group of employees, a service line, a group of service lines, a hospital facility or a group of hospital facilities in a given region, to name a few examples. SOM techniques can also be employed to predict the classification, type, or grouping of a particular pending event leveraging the attributes or inputs from an already existing data set of events, for example.

Exemplary Implementation

Figure 6:
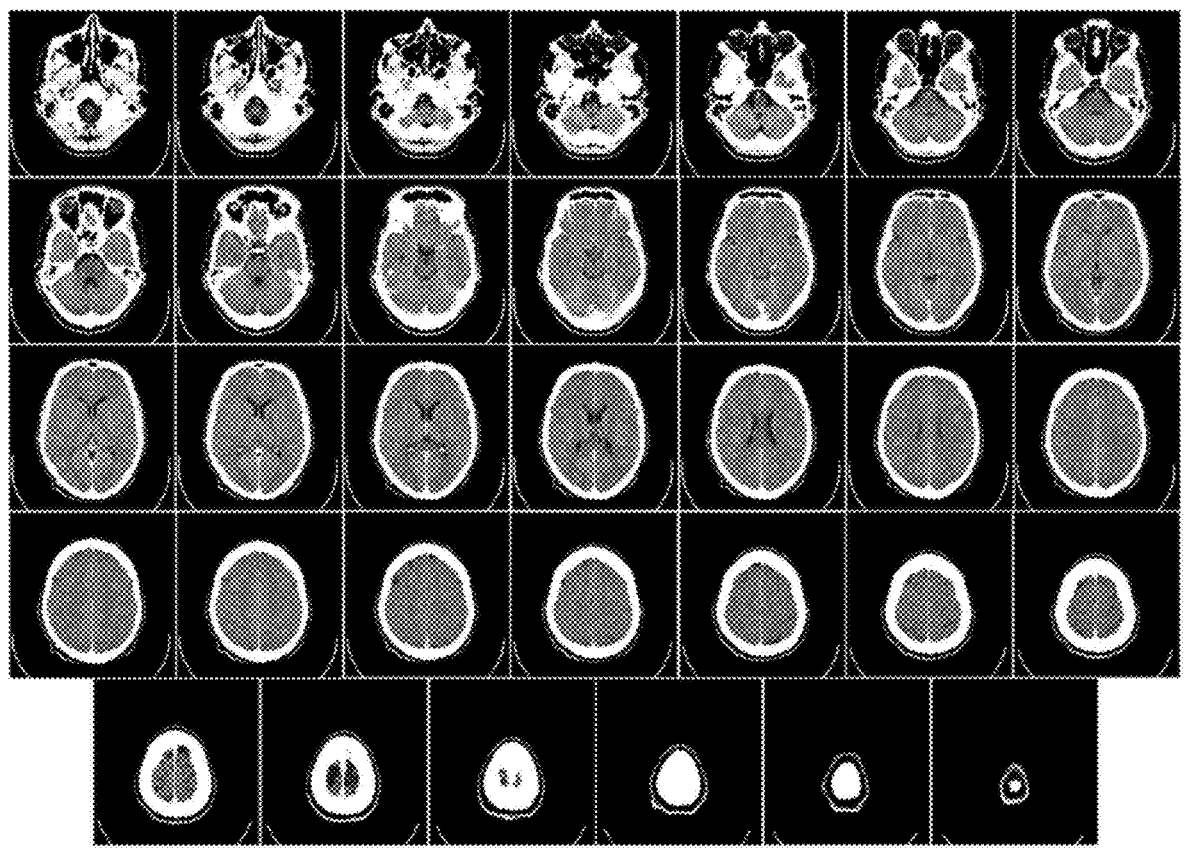
FIG. 6 is an example CT scan of human brain from base of the skull to the top.

An exemplary implementation will be discussed for a case in which an NNM is created, trained and validated to determine whether a patient event is likely to require surgical intervention. The patient event is a CT scanning of a patient head using a series of x-rays of the head taken from different directions. Typically used for quickly viewing brain injuries, CT scanning uses a computer program that performs a numerical integral calculation (the inverse Radon transform) on the measured x-ray series to estimate how much of an x-ray beam is absorbed in a small volume of the brain. Typically, the information is presented as a series of cross sections of the brain. Referring to FIG. 6, a CT of human brain is performed from base of the skull to top with intravenous contrast medium.

Deep Learning

The system employs deep-learning to achieve automated diagnostic predictions. The backend devices can store trained models capable of ingesting de-novo images, automate the preprocessing of them, and the processing of them with the system's trained models in order to make diagnostic predictions.

For the sake of example, one implementation the system can employ is one similar to the Recurrent Attention DenseNet (RADnet) architecture described by Monika Grewal et. al. Grewal et. al. utilizes a DenseNet baseline Convolutional Neural Network (CNN) and bi-directional Long-Term Short Term Memory (LSTM) network. The DenseNet architecture's focus is "learning" slice level features while the bidirectional LSTM is leveraged combine "intra" slice dependencies. This process is further augmented via the inclusion of an attention mechanism which allows the neural network to increase its focus towards "salient" features.

Figure 7:
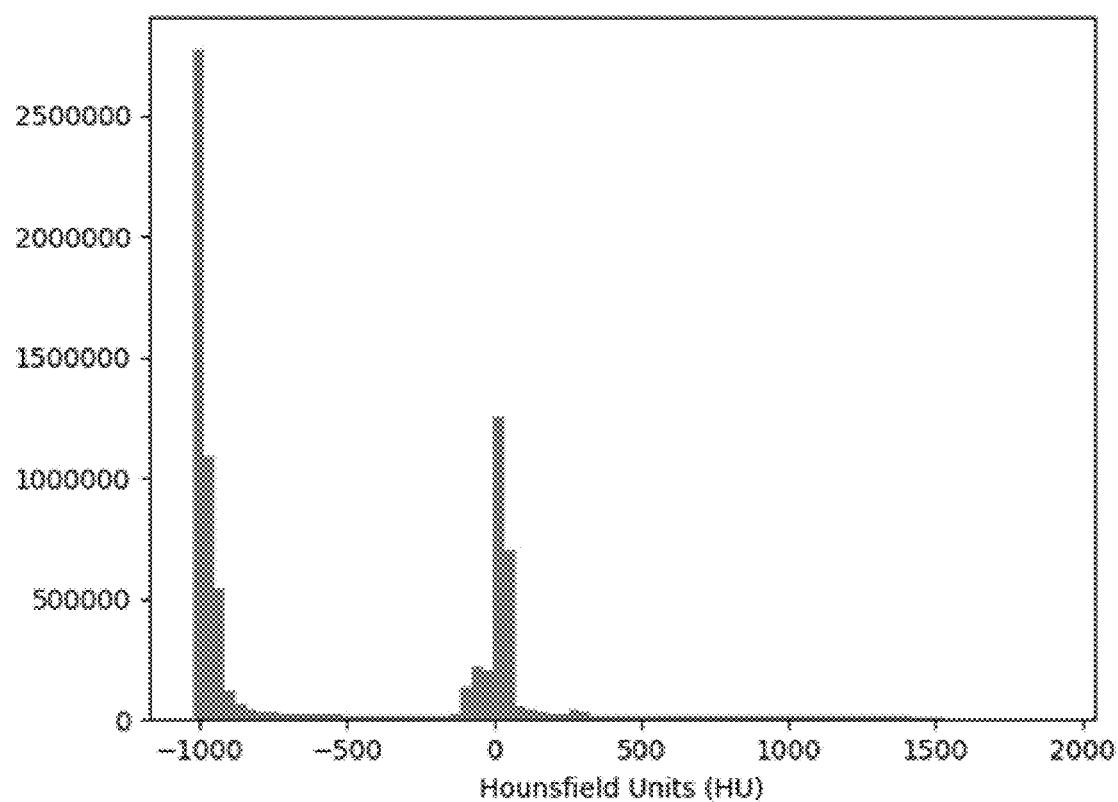
FIG. 7 is a histogram showing distributions of HUs from exemplary CT scan.
Figure 8A:
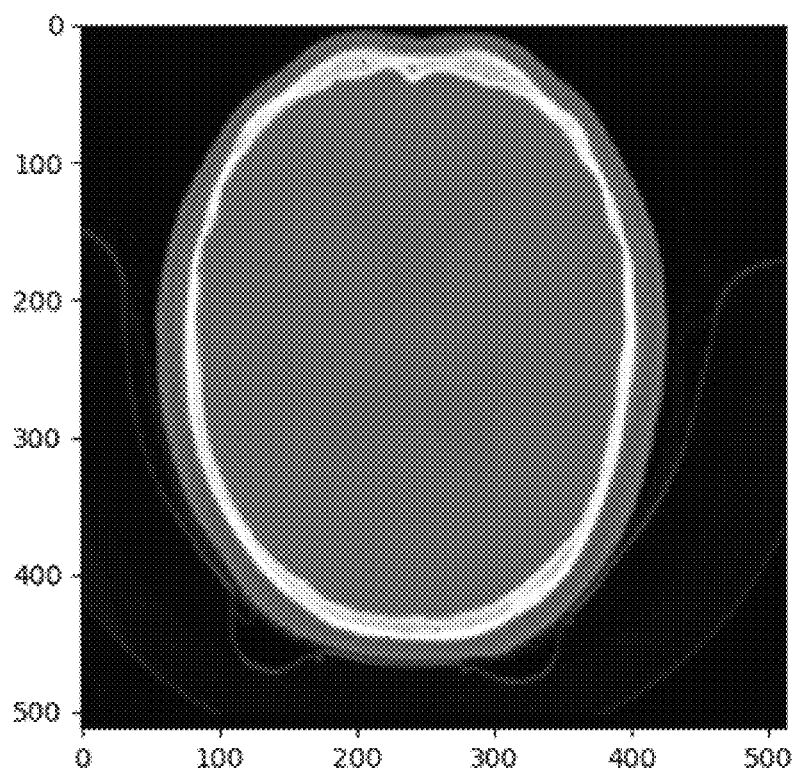
FIGS. 8A-8D show axial sections from an exemplary CT head scan.
Figure 8B:
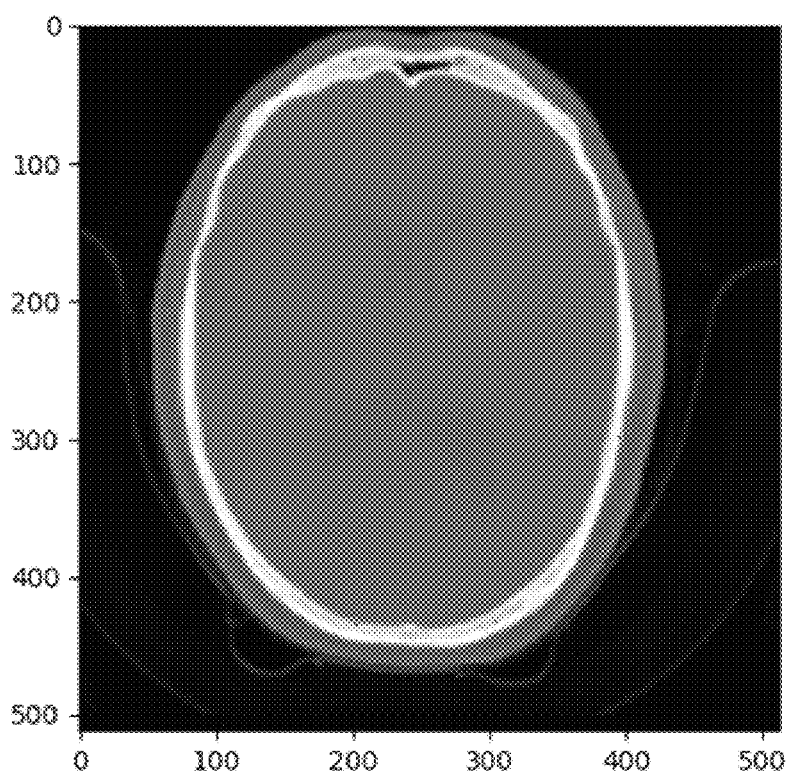
Figure 8C:
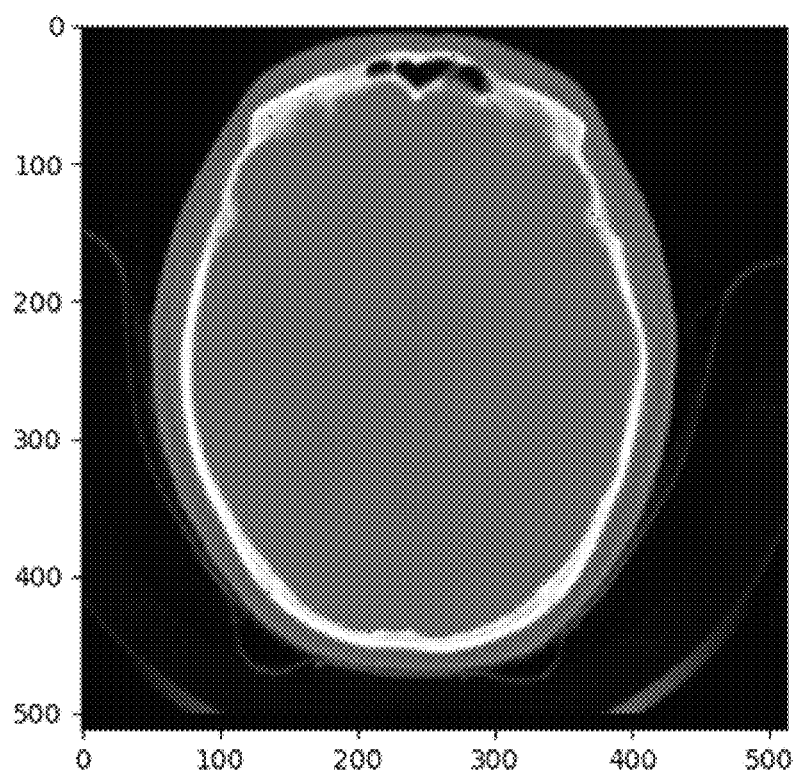
Figure 8D:
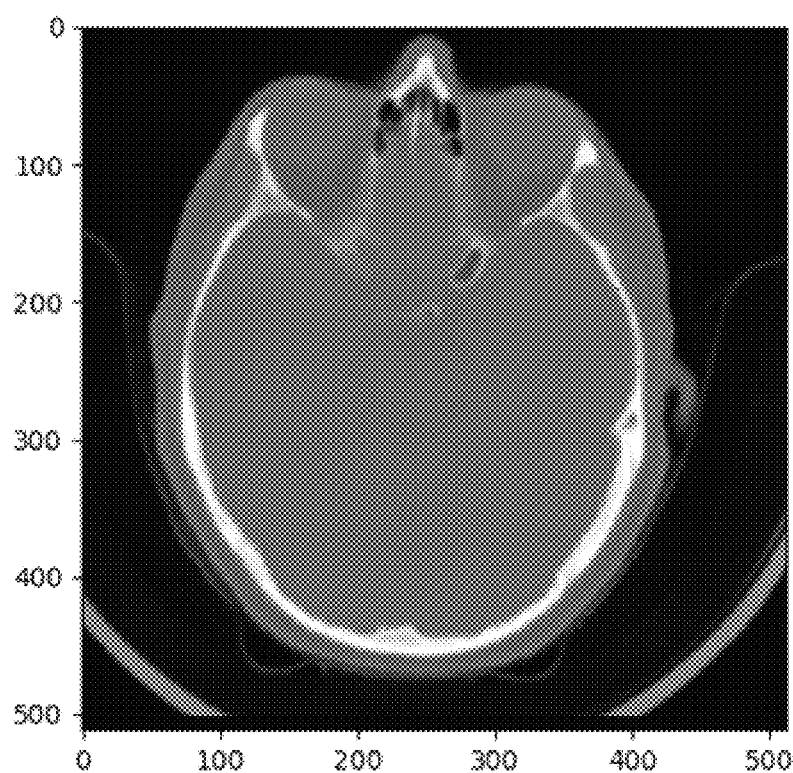
Figure 8E:
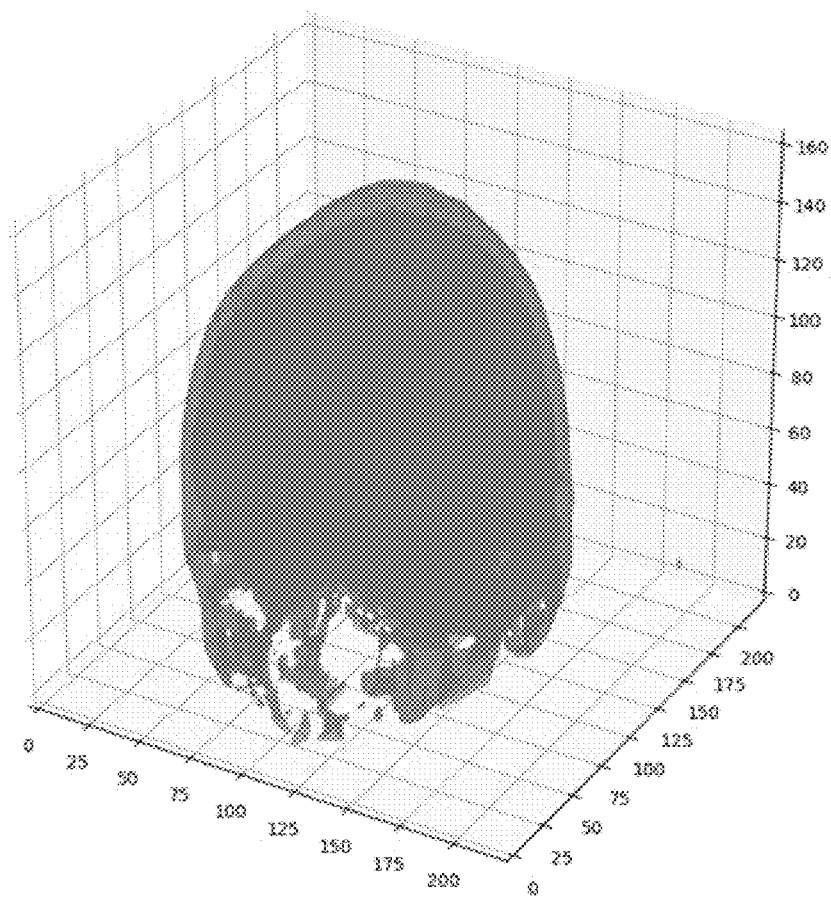
FIG. 8E shows an example 3D reconstruction of CT head.

Steps:

Image Acquisition:

DCM (DICOM) images are acquired (series of images in a CT Scan of the Brain, which is sequential x-rays taken at increments through, in this case, the patient's brain) and stored in memory. The array of pixel intensity data included in the DICOM files can be read into an array in memory. The rescale intercept and the rescale slope for each slice can also be read from the header information in the DICOM files and put into memory. Using the previously described methodology (U=m×SV+b, where U is the CT Number, m is the rescale slope, b is the rescale intercept and SV is the persisted or stored value), the intensity data (SV) for each pixel, the rescale slope (m), and the rescale intercept (b) . . . the CT Number (U) can then be derived/calculated; this value will then be in Hounsfield Units. FIG. 7 shows a histogram showing distribution of HUs from exemplary CT Scan of the Head generated using Matplotlib, a Python plotting library, prior to pre-processing Referring to FIGS. 8A-8D, axial sections from an exemplary CT Scan of the Head Generated using Matplotlib, a Python plotting library, prior to pre-processing; note 512× 512 pixel dimensions. Referring to FIG. 8E, a 3D reconstruction of CT head generated with Matplotlib, a Python plotting library.

Preprocessing:

Resampling

Depending on the machine and acquisition protocol, different CT scans can have different "intra-slice" distances between sequential x-rays, for example every 2.5 millimeters or every 1.5 millimeters.

Pixel spacing is the physical distance (in the patient) between the centers of each two-dimensional pixel in the acquired image and is specified by two numeric values. The pixel spacing between different CT scans of the brain can differ, for example one may have a pixel spacing of 0.5 millimeters×0.5 millimeters whereas another might have a pixel spacing of 0.725 millimeters×0.725 millimeters. This variation in pixel spacing and "intra-slice" distances can pose problems when doing automated analysis, for example with convolutional neural networks. To correct for these differences between patient studies, all scans in the training, validation data sets and any scans subsequently passed to the trained models are resampled to a consistent isotropic resolution, for example 1 millimeter×1 millimeter×1 millimeter resulting, typically, in a field-of-view in-plane of approximately 250 millimeters×250 millimeters. The system can be configured to employ any method of accomplishing this.

Sample Python Code for Resampling Using NumPy and ScyPy

```
def resample(rawImage, ctHead, resampledSpacing=[1,1,
    1]):
    thickness=ctHead[0].SliceThickness
    array=[thickness, ctHead[0].PixelSpacing[0], ctHead
        [0].PixelSpacing[1]]
    currentSpacing=numpy.array(array,
        dtype=numpy.float32)
    multiplier=currentSpacing/resampledSpacing
    resampledShape=rawImage.shape*multiplier
``` resampledShape=numpy.round(resampledShape)
actualMultiplier=resampledShape/rawImage.shape
resampledSpacing=currentSpacing/actualMultiplier
image=scipy.ndimage.interpolation.zoom(rawImage,
  actualMultiplier, mode='nearest')
return image, resampledSpacing "Windowing" Image Series from Patient Studies and Normalizing the Data Windowing, also called grey-scale mapping, contrast sketching, histogram modification, or contrast enhancement, is a means of manipulating the gray scale component of an image by changing the range of HUs. Thus, windowing changes the appearance of a given scan image allowing different structures to be highlighted. Said another way, windowing adjusts the brightness of a given scan image via the window width (range of HUs included) and the window level or window center (midpoint of the range of HUs included).

As described earlier, the data from a CT scan correlating with different parts of the body (i.e. the brain structures or blood), is found in the data on a CT scan at/within different HU ranges. Thus, as a part of pre-processing, data that is not within the HU range of findings/structures of interest can be ignored. Said another way, the CT scan can be "windowed" to include only data of interest. For example, to include intracranial structures of the brain and any blood, as might occur in the case of a subarachnoid hemorrhage or subdural hematoma, a HU range of 0-100, or something similar, might be ideal.

This windowing is important as a wider window width results in the different attenuations of soft tissue becoming obscured, whereas a narrower window width is ideal to examine areas of similar attenuation, such as soft tissue.

The inventive system can be configured for any particular HU range, depending on the specific application and to optimize the training of the models.

In addition, to "windowing" the studies, during pre-processing, the data acquired can also be further normalized (in addition to resampling); namely the HU levels can be converted to the range 0-1. This normalization of input data can speed up the training process. Data is normalized as follows, where $x_i=(x_1, \ldots, x_n)$ and $z_i$ is the $i^{th}$ normalized data:

$$z_i = (x_i - \min(x))/(\max(x) - \min(x))$$

Any particular implementation of this process can be employed by the system. The below is one such exemplary implementation where the scan in windowed to an HU range of 0-100 and the HU are converted to a range of 0-1.

Sample Python Code for Windowing and Normalizing CT Scan Data

```
#exemplary embodiment windowing image for brain/
  blood
_lowerWindowBoundary=0 #HU
_upperWindowBoundary=100 #HU
def normalizeCtHead(img):
    img=(img-_lowerWindowBoundary)/(_upperWin-
      dowBoundary-_lowerWindowBoundary)
    img [img>1]=1.
    img [img<0]=0.
    return img
```

Zero-Centering

Centering a variable entails subtracting the mean of the variable from each value. This makes the average of the new values zero. Said another way, this results in a linear transformation of the data that moves the data so its center is the origin. Some call this finding the "natural coordinate system" for the data. This also ensures that the standard deviation of the data is normalized to one. Generally, non-linear analysis or operations do better when the data is zero-centered. Zero-centering data also makes it easier to reason about variation. This is also an approach to isolate the primary components of independent variation because that variation will lie on a different axis.

Thus, the system can employ zero-centering as part of the pre-processing of images to optimize the data prior to training. This can be implemented by the inventive system by passing in a zero-centering function.

Sample Python Code for Zero-Centering CT Scan Data

```
#"mean pixel" is the average pixel value (shown here as
a step after normalization) for all images in image set
  _meanPixel=0.25 #Heuristic for exemplary embodiment
  def zeroCenterCtHead(img):
      img=img-_meanPixel
      return img
```

Figure 9:
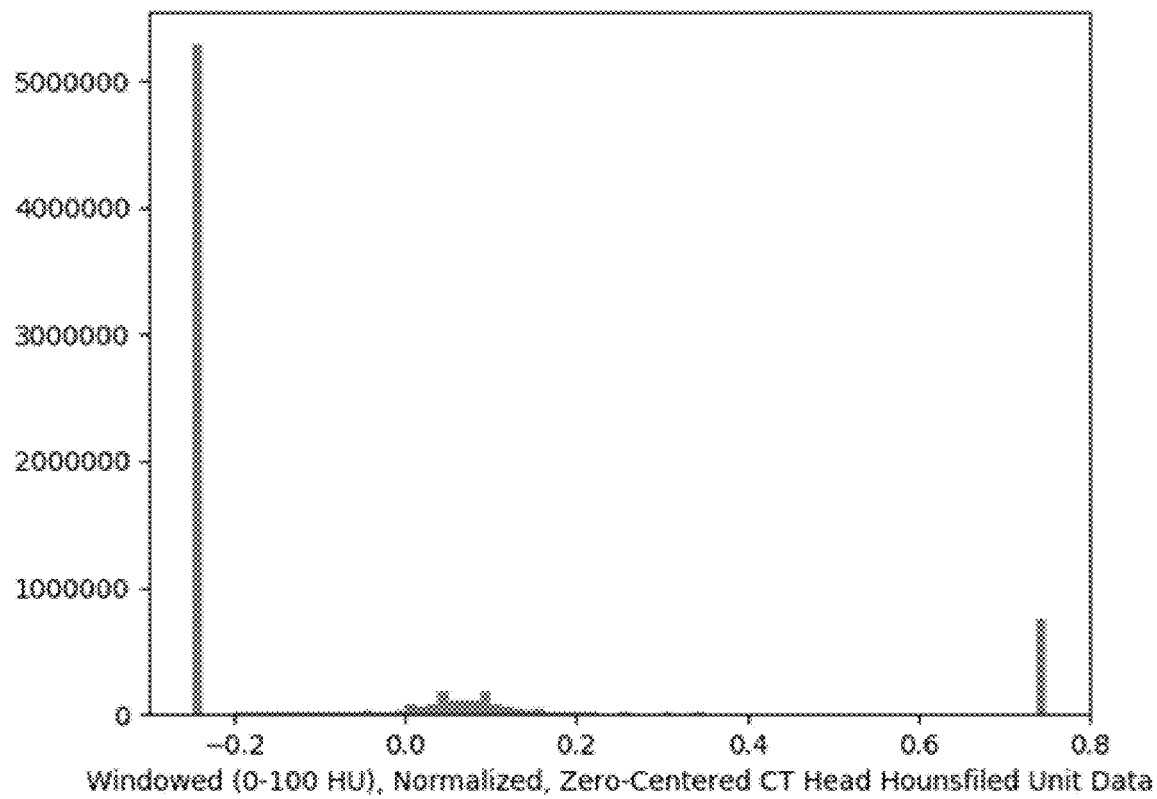
FIG. 9 is a histogram showing windowed distribution of HUs from exemplary CT Scan of the Head.
Figure 10A:
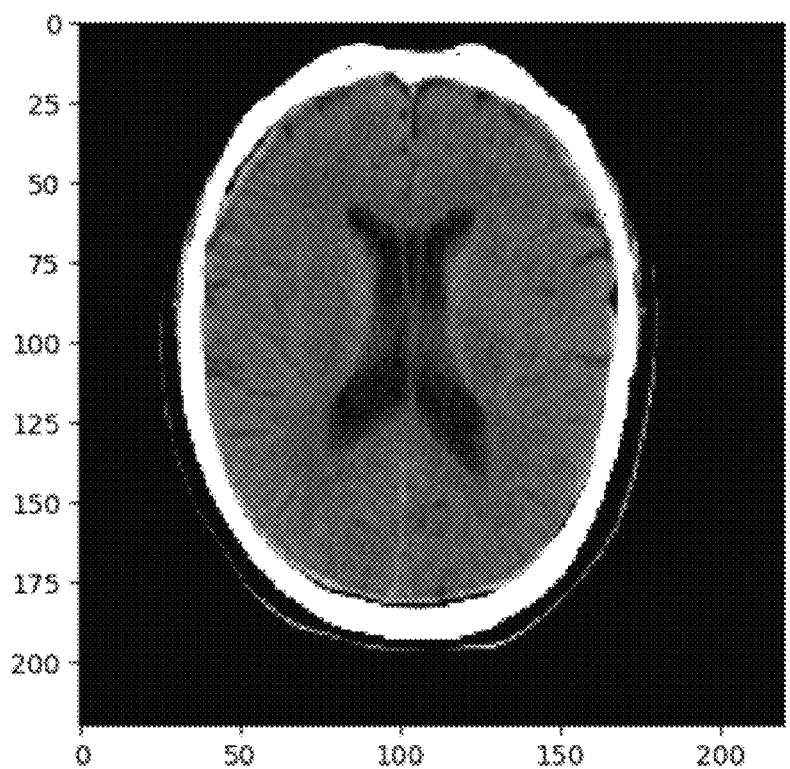
FIGS. 10A-10D show axial sections from an exemplary CT scan.
Figure 10B:
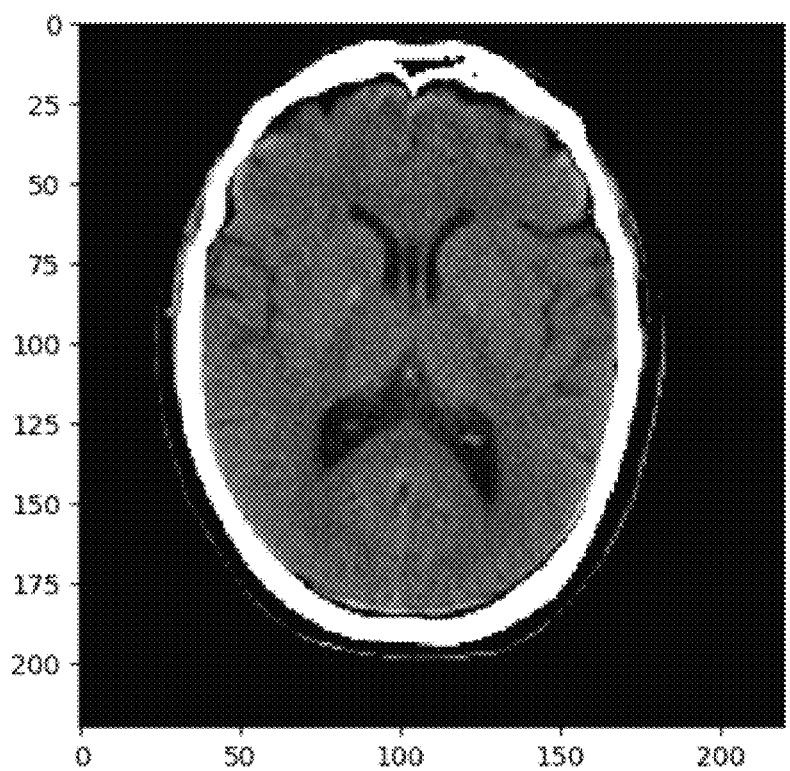
Figure 10C:
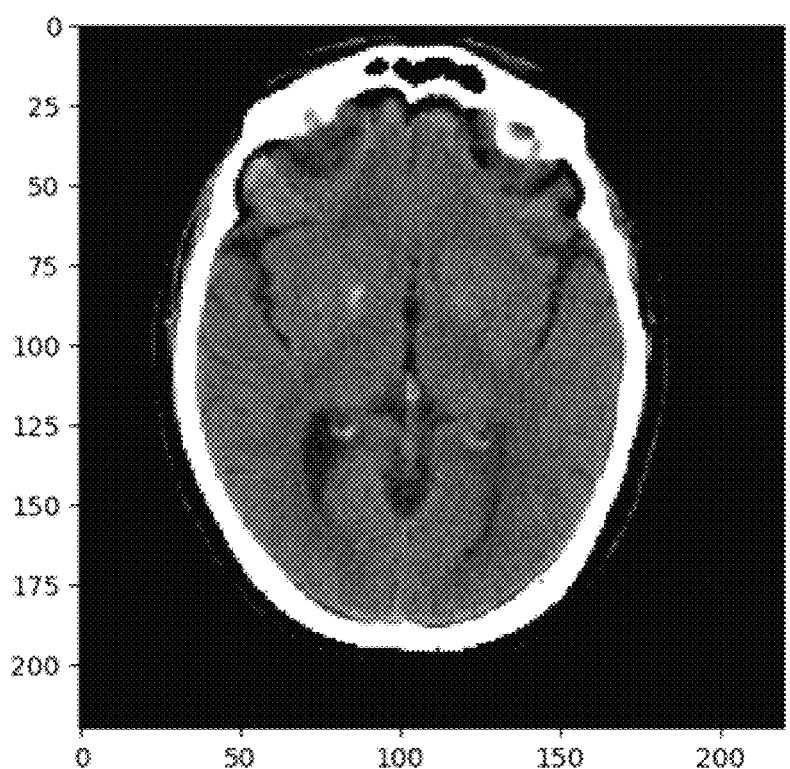
Figure 10D:
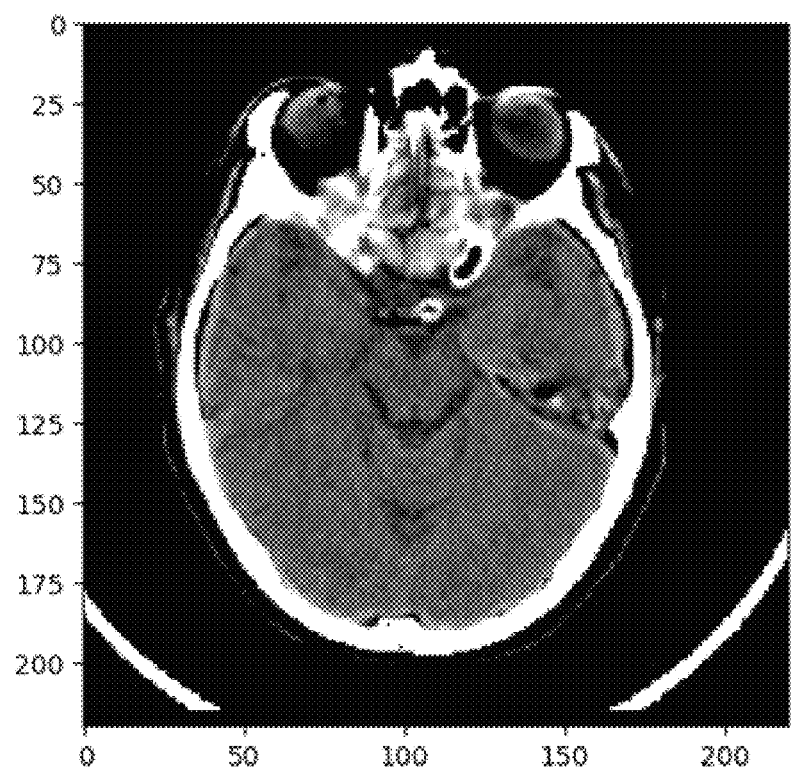

FIG. 9 illustrates a histogram showing distribution of HUs from exemplary CT Scan of the Head generated using Matplotlib, a Python plotting library, after pre-processing. FIGS. 10A-10D illustrate axial sections from an exemplary CT Scan of the Head Generated using Matplotlib, a Python plotting library, prior to pre-processing; note 220×220 pixel dimensions.

Other Pre-Processing

While, herein, several pre-processing steps have been described this is exemplary and is in no way intended to limit the scope and extent of pre-processing steps and types the inventive system may take. Other examples, include but are not limited to, principal components analysis (PCA)—a dimensionality reduction algorithm—and whitening, also referred to by some as sphering, the goal of which is to reduce the redundancy of the input data. Again, the system can be configured to carry out any number of pre-processing steps.

Image Processing:

The server processes the images from CT Scans of the Brain, along any orientation using training algorithm and machine learning model. Images are stacked together to create a 3D point cloud and the inventive system processes the images using 3D Convolutional Neural Networks (CNN). As previously mentioned, the system can employ other methods alone or in combination, such as examining the data sequentially by passing it through a recursive neural network like a recurrent neural network (RNN) or (long-short term memory) LSTM network with hidden layers from pre-trained models like DenseNet, which is the approach used by Grewal et al in their Recurrent Attention DenseNet (RADNet).

The system can employ a dynamic way of managing class imbalance in the dataset, which is very common for medical datasets. For example, after every few epochs, accuracy is calculated on the validation set for all classes. Then a new training subset is created where classes with lower accuracy are present in higher proportions.

Training and Validation Data Set Preparation

The following is an exemplary description of the training and validation data set preparation for use in training the models. CT scans of the brain are reviewed, preferably, by three or more board certified radiologists, neuro-radiologists, neurosurgeons, and/or neurologists, and annotated at the slice-level (including class-labels and segmentation contours) for the presence of hemorrhage and the radiology reports for each CT scan are reviewed for finding of acute hemorrhage. This latter step can be used in model training as part of the attention mechanism previously described.

Model Architecture, Training and Validation

The system has the flexibility to be tooled with any variety of model architectures and model training approaches which allow it to adopt and evolve over time as the field advances and new techniques are validated.

For example, the system can be tooled to leverage the following exemplary architecture and model training process described by Monika Grewal et. al. of a 40-layer DenseNet architecture with three dense blocks as the baseline network and three auxiliary tasks to compute binary segmentation of the hemorrhagic regions.

The auxiliary task branches are forked after the last concatenation layer in each dense block and consist of a single module of 1×1 convolutional layer followed by a deconvolution layer to unsample the feature maps to original image size.

The final loss is defined as the weighed sum of the cross-entry loss for main classification task and losses for three auxiliary tasks, so called DenseNet-A modification.

The RADnet architecture models the inter-slice dependencies between 2D slices of the CT Scans of the Brain by incorporating bidirectional LSTM layer to DenseNet-A.

The output of the global pool layer in the original architecture is passed through a single bidirectional LSTM layer before sending to fully connected layer for final prediction.

Training

RADnet model is trained with sequences of multiple 2D slices allowing predictions for a single slice while taking into account the 3D context in a "small neighborhood."

Stochastic gradient descent for 60 epochs with initial learning rate of 0.001 and 0.9 momentum. The momentum rate is reduced to 1/10 of the original value after 1/3 and 2/3 of the training finished. The network weights are initialized using norm initialization as described by Kaimineng He et. al. The data set is augmented using rotation and horizontal flipping to balance positive and negative class ratios along with increasing generalizability of the model. The hyperparameters are tuned to give the best performance on the validation set.

Evaluation

The system aggregates slice level predictions from RADnet to infer CT Scan of the brain level predictions.

The trained models can be configured such that CT scans of the brain are declared positive based on specified criteria. For example, in the case of intracranial hemorrhage, if the deep learning models predicted hemorrhage in three or more consecutive slices, the scan can be declared to have a high probability of being positive for an intracranial hemorrhage. The trained models can generate other output values besides the presence of blood as just described for predicting an outcome (requirement for surgical intervention). For example, the volume or location of blood including distinguishing intra-axial from extra-axial bleeds; the displacement of the brain (i.e. midline-shift, sub-falcine or temporal herniation, ventricular effacement and or displacement, etc.); or diagnosis or pattern/type of bleed (traumatic subarachnoid hemorrhage, aneurysmal subarachnoid hemorrhage, subdural hematoma, epidural hematoma, etc.) can be generated from trained models based upon the imaging patterns. Further, other input attributes can include data from electronic health records system, for example the history of the patient that led to their presentation to the medical facility, and other hospital information systems, including whether or not patients with similar objective imaging findings actually were taken to surgery. In optimizing the models during the training process, this is one of the factors that can be refined to minimize the global error and maximize the quality of the predictions.

Performance of the system during training and validation is determined by comparing predictions to known interpretation of the images by board-certified radiologists, neuro-radiologists, neurosurgeons, and/or neurologists.

While only certain features of the invention have been illustrated and described herein, many modifications and changes will occur to those of ordinary skill in the art. The following claims are intended to cover all such modifications and changes.

What is claimed is:

1. A method for predicting an outcome associated with a new patient event, the method comprising:
   receiving a plurality of input attributes of the new patient event;
   performing pre-processing on the plurality of input attributes to generate an input data set;
   generating an output value from a trained model based upon the input data set;
   classifying the output value into a surgical intervention risk category to predict the outcome;
   storing a plurality of past patient events, each of the plurality of past patient events including a plurality of input attributes and a quantifiable outcome; and
   training a neural network model (NNM) to generate the trained model, wherein the training of the NNM includes:
   performing pre-processing on the plurality of input attributes for each of the plurality of past patient events to generate a plurality of input data sets;
   dividing the plurality of past patient events into a first set of training data and a second set of validation data;
   iteratively performing a machine learning algorithm (MLA) to update synaptic weights of the NNM based upon the training data; and
   validating the NNM based upon the second set of validation data.

2. The method of claim 1, wherein:
   the NNM includes an input layer, output layer, and a plurality of hidden layers with a plurality of hidden neurons; and
   each of the plurality of hidden neurons includes an activation function, the activation function is one of:
   (1) the sigmoid function $f(x)=1/(1+e-x)$;
   (2) the hyperbolic tangent function $f(x)=(e2x-1)/(e2x+1)$; and
   (3) a linear function $f(x)=x$,
   wherein x is a summation of input neurons biased by the synoptic weights.

3. The method of claim 1, wherein the NNM is one or more of a feed forward structure Neural Network; Convolutional neural network (CNN); ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), and Radial Basis Function Network.

4. The method of claim 1, wherein the performing of the MLA includes measuring a global error in each training iteration for the NNM by:
   calculating a local error, the local error being a difference between the output value of the NNM and the quantifiable outcome;

calculating the global error by summing all of the local errors in accordance with one of:

(1) Mean Square Error (MSE) formula $$\frac{\Sigma_n E^2}{n};$$

(2) Root Mean Square Error (RMS) formula $$\sqrt{\frac{\Sigma_n E^2}{n}};$$

and (3) Sum of Square Errors (ESS) formula $$\frac{\Sigma_n E^2}{2},$$

wherein represents a total number of the past patient events and E represents the local error.

5. The method of claim 1, wherein the new patient event is an imaging study performed on a patient, and the plurality of input attributes include a plurality of Hounsfield unit (HU) values associated with an image of the imaging study.

6. The method of claim 5, wherein the imaging study includes a computed tomography (CT) scan of the head of the patient using series of x-rays of the head taken from many different directions, and the image is a DICOM image.

7. The method of claim 1, wherein:
the receiving of the plurality of input attributes of the new patient event further includes receiving a Digital Imaging and Communications in Medicine (DICOM) imaging file including patient identification and an array of pixel intensity data associated with a computed tomography (CT) scan;
the performing of pre-processing on the plurality of input attributes to generate an input data set further comprises further includes windowing values of the pixel intensity data outside of a predetermined range;
the generating an output value from a trained model based upon the input data set further includes generating a Hounsfield unit (HU) pixel intensity value of a pixel; and
the classifying the output value into a surgical intervention risk category to predict the outcome further includes classifying a patient event based upon the HU pixel intensity value.

8. The method of claim 6, wherein:
the generating an output value from a trained model based upon the input data set further includes generating a Hounsfield unit (HU) pixel intensity value of a pixel; and
the classifying the output value into a surgical intervention risk category to predict the outcome further includes classifying a patient event as clotted when the HU pixel intensity value is greater than or equal to 50 and less than or equal to 75.

9. The method of claim 6, wherein:
the generating an output value from a trained model based upon the input data set further includes generating a Hounsfield unit (HU) pixel intensity value of a pixel; and
the classifying the output value into a surgical intervention risk category to predict the outcome further includes classifying the patient event as subdural hematoma when the HU pixel intensity value is greater than or equal to 75 and less than or equal to 100 within 24 hours from date of imaging study.

10. The method of claim 6, wherein:
the generating an output value from a trained model based upon the input data set further includes generating a Hounsfield unit (HU) pixel intensity value of a pixel; and
the classifying the output value into a surgical intervention risk category to predict the outcome further includes classifying the patient event as subdural hematoma when the HU pixel intensity value is greater than or equal to 65 and less than or equal to 85 within 72 hours from date of imaging study.

11. The method of claim 6, wherein:
the generating an output value from a trained model based upon the input data set further includes generating a Hounsfield unit (HU) pixel intensity value of a pixel; and
the classifying the output value into a surgical intervention risk category to predict the outcome further includes classifying the patient event as subdural hematoma when the HU pixel intensity value is greater than or equal to 35 and less than or equal to 40 within 10 days from date of imaging study.

12. A method for predicting an outcome associated with a new patient event, the method comprising:
receiving a plurality of input attributes of the new patient event;
performing pre-processing on the plurality of input attributes to generate an input data set;
generating an output value from a trained model based upon the input data set, wherein the trained model is a trained Self-Organizing Map (SOM) including a plurality of network nodes arranged in a grid or lattice and in fixed topological positions, an input layer with a plurality of input nodes representing the input attributes of the past patient events, wherein each of the plurality of input nodes is connected to all of the plurality of network nodes by a plurality of synaptic weights;
storing a plurality of past patient events, each of the plurality of past patient events including a plurality of input attributes and a quantifiable outcome;
performing pre-processing on the plurality of input attributes for each of the plurality of past patient events to generate a plurality of input data sets; and
training a SOM to generate the trained model, wherein the training of the SOM includes:
initializing values of the plurality of synaptic weights to random values,
randomly selecting one past patient event and determining which of the plurality of network nodes is a best matching unit (BMU) according to a discriminant function, wherein the discriminant function is a Euclidean Distance; and
iteratively calculating a neighborhood radius associated with the BMU to determine neighboring network nodes for updating, and updating values of synoptic weights for neighboring network nodes within the calculated neighborhood radius for a fixed number of iterations to generate the trained model; and
classifying the output value into a surgical intervention risk category to predict the outcome.

13. The method of claim 12, further including generating another SOM including the plurality of input attributes to reduce dimensionality.

14. The method of claim 1, wherein the receiving the plurality of input attributes of the new patient event further includes receiving data associated with an imaging study.

15. A computer implemented method for predicting a diagnosis associated with a new patient event based upon computerized tomography (CT) scan images, the method comprising:
- receiving a plurality of input attributes including intensity values in Hounsfield units of pixels in the CT scan images;
- performing pre-processing on the plurality of input attributes to generate an input data set;
- generating an output value from a trained model stored in a non-transitory storage device associated with a server device based upon the input data set;
- predicting the diagnosis based upon the output value;
- storing a plurality of past patient events, each of the plurality of past patient events including a plurality of input attributes and a quantifiable outcome;
- training a neural network model (NNM) to generate the trained model, wherein the training of the NNM includes:
  - performing pre-processing on the plurality of input attributes for each of the plurality of past patient events to generate a plurality of input data sets;
  - dividing the plurality of past patient events into a first set of training data and a second set of validation data;
  - iteratively performing a machine learning algorithm (MLA) to update synaptic weights of the NNM based upon the training data; and
  - validating the NNM based upon the second set of validation data.

16. A computer implemented method for predicting an outcome associated with a new patient event, the method comprising:
- receiving a plurality of input attributes of the new patient event;
- performing, at a server device, pre-processing on the plurality of input attributes to generate an input data set;
- generating an output value from a trained model stored in a non-transitory storage device associated with the server device based upon the input data set;
- classifying the output value into a surgical intervention risk category to predict the outcome;
- storing a plurality of past patient events, each of the plurality of past patient events including a plurality of input attributes and a quantifiable outcome;
- training a neural network model (NNM) to generate the trained model, wherein the training of the NNM includes:
  - performing pre-processing on the plurality of input attributes for each of the plurality of past patient events to generate a plurality of input data sets;
  - dividing the plurality of past patient events into a first set of training data and a second set of validation data;
  - iteratively performing a machine learning algorithm (MLA) to update synaptic weights of the NNM based upon the training data; and
  - validating the NNM based upon the second set of validation data.

\* \* \* \* \*